(12) United States Patent
Larochelle et al.

(10) Patent No.: US 11,565,128 B2
(45) Date of Patent: Jan. 31, 2023

(54) METHOD FOR LIGHT TREATMENT PLANNING USING LOCATION-INFORMED MODELS

(71) Applicant: Trustees of Dartmouth College, Hanover, NH (US)

(72) Inventors: Ethan Phillip M. Larochelle, Thetford Center, VT (US); Brian W. Pogue, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 323 days.

(21) Appl. No.: 16/916,852

(22) Filed: Jun. 30, 2020

(65) Prior Publication Data

US 2021/0001149 A1  Jan. 7, 2021

Related U.S. Application Data

(60) Provisional application No. 62/869,107, filed on Jul. 1, 2019.

(51) Int. Cl.
*A61N 5/10* (2006.01)
*A61N 5/06* (2006.01)

(52) U.S. Cl.
CPC ........... *A61N 5/1031* (2013.01); *A61N 5/062* (2013.01); *A61N 5/1048* (2013.01); *A61N 2005/0627* (2013.01); *A61N 2005/1034* (2013.01)

(58) Field of Classification Search
CPC .............. A61N 5/062; A61N 2005/063; A61N 2005/0628; A61N 5/0603; A61B 2034/2061; A61B 90/37; G16Z 99/00; G16H 50/50; G02B 6/262; G02B 6/04; G02B 6/02057

See application file for complete search history.

(56) References Cited

FOREIGN PATENT DOCUMENTS

JP       2015511525 A  *  4/2015

OTHER PUBLICATIONS

Mclellan, Luke & Morelli, Marco & Simeone, Emilio & Khazova, Marina & Ibbotson, Sally & Eadie, Ewan. (2020). SmartPDT®: smartphone enabled real-time dosimetry via satellite observation for daylight photodynamic therapy. 10.13140/RG.2.2.36093.18402.
O'Mahoney, P. and Eadie, E. (2020), Bring the Sunshine Indoors: Easy Dosimetry for Indoor Daylight Photodynamic Therapy. Photochem Photobiol, 96: 434-436. <https://doi.org/10.1111/php.13192>.
(Continued)

*Primary Examiner* — Don K Wong
(74) *Attorney, Agent, or Firm* — Shackelford, Bowen, McKinley & Norton, LLP

(57) ABSTRACT

In an embodiment, the present disclosure pertains to a method of determining optimal parameters for application of light from a light source to a tissue. In general, the method includes one or more of the following steps of: (1) utilizing an algorithm to generate results related to estimating light flow from the light source into the tissue; and (2) utilizing the results to determine optimal parameters for applying the light source to the tissue. In some embodiments, the method of the present disclosure further includes the step of: (3) applying the light source to the tissue using the optimal parameters; and (4) treating a condition associated with the tissue.

33 Claims, 20 Drawing Sheets

(56) References Cited

OTHER PUBLICATIONS

LaRochelle EPM, Chapman MS, Maytin EV, Hasan T, Pogue BW. Weather-informed Light-tissue Model-Based Dose Planning for Indoor Daylight Photodynamic Therapy. *Photochem Photobiol.* 2020;96(2):320-326. doi:10.1111/php.13170.

Heppt MV, Steeb T, Berking C. Photodynamic therapy 'to go'—a strengths, weaknesses, opportunities and threats analysis. Journal of the European Academy of Dermatology and Venereology : JEADV. Dec. 2019;33(12):e447-e449. DOI: 10.1111/jdv.15772.

LaRochelle EPM, Marra K, LeBlanc RE, Chapman MS, Maytin EV, Pogue BW. Modeling PpIX effective light fluence at depths into the skin for PDT dose comparison. Photodiagnosis Photodyn Ther. Mar. 2019;25:425-435. doi: 10.1016/j.pdpdt.2019.01.022. Epub Jan. 25, 2019. PMID: 30685548.

De Souza ALR, LaRochelle E, Marra K, Gunn J, Davis SC, Samkoe KS, Chapman MS, Maytin EV, Hasan T, Pogue BW. Assessing daylight & low-dose rate photodynamic therapy efficacy, using biomarkers of photophysical, biochemical and biological damage metrics in situ. Photodiagnosis Photodyn Ther. Dec. 2017;20:227-233. doi: 10.1016/j.pdpdt.2017.10.005. Epub Oct. 14, 2017. PMID: 29037911; PMCID: PMC5718943.

Marra, K., LaRochelle, E.P., Chapman, M.S., Hoopes, P.J., Lukovits, K., Maytin, E.V., Hasan, T. and Pogue, B.W. (2018), Comparison of Blue and White Lamp Light with Sunlight for Daylight☐Mediated, 5☐ALA Photodynamic Therapy, in vivo. Photochem Photobiol, 94: 1049-1057. <https://doi.org/10.1111/php.12923>.

Ethan Philip M. LaRochelle, Alberto J. Ruiz, Robert E. LeBlanc, Edward V. Maytin, Tayyaba Hasan, M. Shane Chapman, and Brian W. Pogue "Weather forecast and light-tissue model based dose planning for daylight PpIX-photodynamic therapy of skin (Conference Presentation)", Proc. SPIE 11070, 17th International Photodynamic Association World Congress, 110705B (Aug. 14, 2019); <https://doi.org/10.1117/12.2525434>.

Ethan Philip M. LaRochelle, Alberto J. Ruiz, M. Shane Chapman, Edward V. Maytin, Tayyaba Hasan, and Brian W. Pogue "Clinical implementation of model-based dose planning for indoor daylight photodynamic therapy of skin (Conference Presentation)", Proc. SPIE 11220, Optical Methods for Tumor Treatment and Detection: Mechanisms and Techniques in Photodynamic Therapy XXIX, 1122006 (Mar. 10, 2020); <https://doi.org/10.1117/12.2543536>.

\* cited by examiner

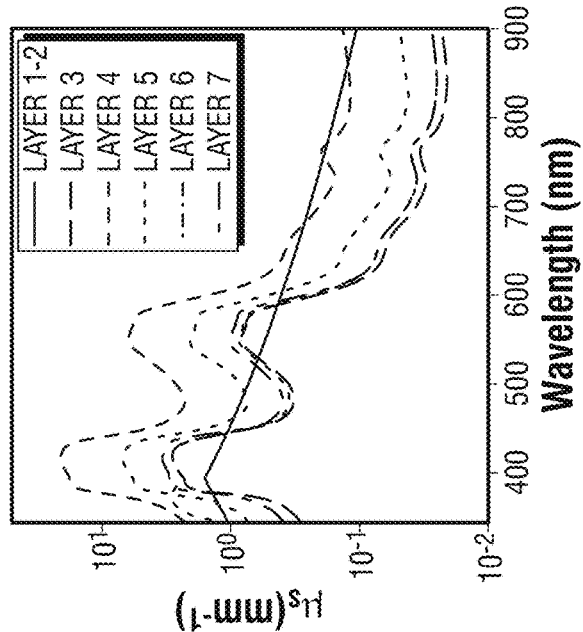
FIG. 4C
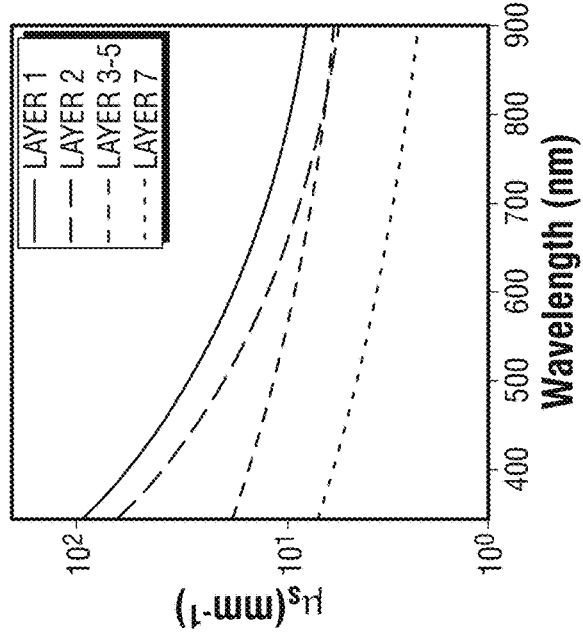
FIG. 4B
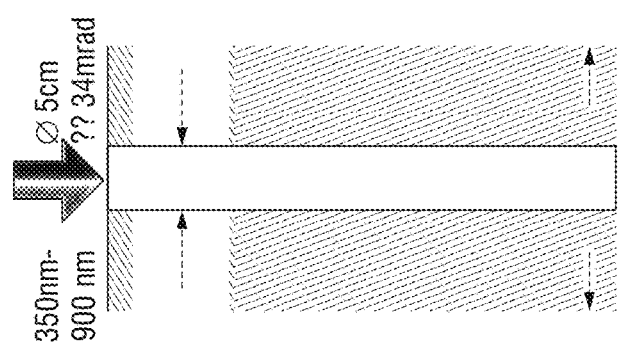
FIG. 4A
| | LAYER 1 (STRATUM CORNEUM) | LAYER 2 (LIVING EPIDERMIS) | LAYER 3 (PAPILLARY DERMIS) | LAYER 4 (UPPER BLOOD NET DERMIS) | LAYER 5 (RETICULAR DERMIS) | LAYER 6 (DEEP BLOOD NET DERMIS) | LAYER 7 (SUBCU. FAT) |
|---|---|---|---|---|---|---|---|
| n | 1.50 | 1.34 | 1.40 | 1.39 | 1.40 | 1.38 | 1.44 |
| g | 0.86 | 0.80 | 0.90 | 0.95 | 0.80 | 0.95 | 0.75 |
FIG. 4D

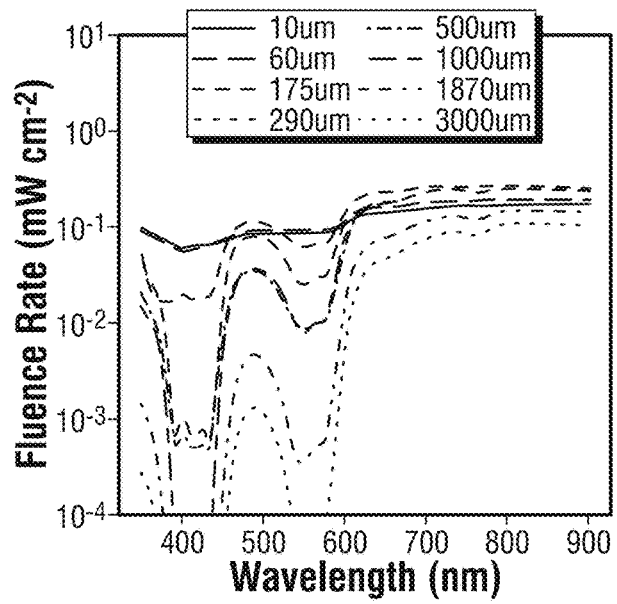
FIG. 5A
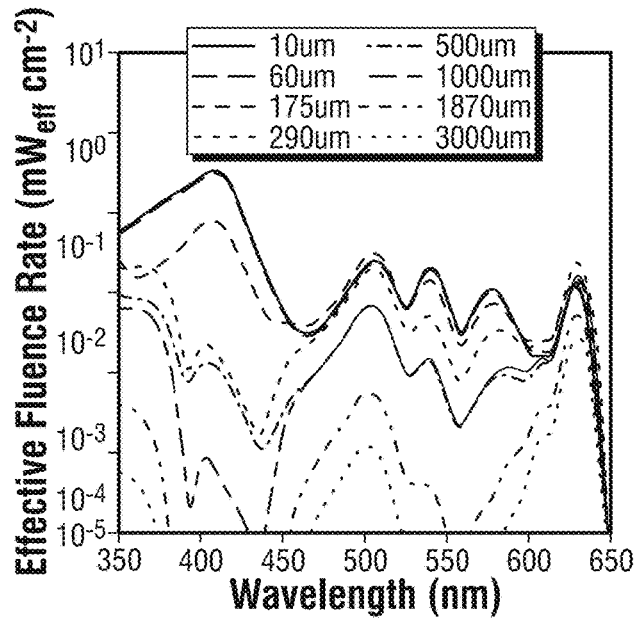
FIG. 5B
STRATUM CORNEUM (20μm)
LIVING EPIDERMIS (80μm)
PAPILLARY DERMIS (150μm)
UPPER BLOOD NET DERMIS (80μm)
RETICULAR DERMIS (1.5mm)
DEEP BLOOD NET DERMIS (80μm)
SUBCUTANEOUS FAT (6mm)
FIG. 5C

| TREATMENT TIME (MINUTES) | MAXIMUM DEPTH OF PDD (mm) |
|---|---|
| 10 | 0.9 |
| 20 | 1.1 |
| 30 | 1.2 |
| 60 | 1.5 |
| 90 | 1.7 |
| 120 | 1.8 |
| 150 | 2.0 |

METHOD FOR LIGHT TREATMENT PLANNING USING LOCATION-INFORMED MODELS

CROSS-REFERENCE TO RELATED APPLICATIONS

This application claims priority to U.S. Provisional Patent Application No. 62/869,107, filed on Jul. 1, 2019. The entirety of the aforementioned application is incorporated herein by reference.

STATEMENT REGARDING FEDERALLY SPONSORED RESEARCH

This invention was made with government support under P01CA084203 awarded by the National Institutes of Health. The government has certain rights in the invention.

BACKGROUND

Typical methods for dose planning for photodynamic therapy (PDT) place large burdens on clinical staff. A simple standardized method for estimating light dose during daylight-PDT is needed to improve inter-site reproducibility while minimizing treatment times and eliminating burdens on clinical staff. Various embodiments of the present disclosure address the aforementioned needs.

SUMMARY

In an embodiment, the present disclosure pertains to a method of determining optimal parameters for application of light from a light source to a tissue. In general, the method includes one or more of the following steps of: (1) utilizing an algorithm to generate results related to estimating light flow from the light source into the tissue; and (2) utilizing the results to determine optimal parameters for applying the light source to the tissue. In some embodiments, the method of the present disclosure further includes the step of: (3) applying the light source to the tissue using the optimal parameters; and (4) treating a condition associated with the tissue.

DESCRIPTION OF THE DRAWINGS

FIG. 3A shows the simulation (dotted) is based on a theoretical uniform spectrum, whereas the other white light sources (solid) are of equal irradiance but based on measured spectral distributions. The narrow-band sources (dashed) are based on clinically-relevant irradiance used in conventional photodynamic therapy (PDT) and the spectrum is nearly equivalent to the FDA-approved Blue-U (Sun/DUSA) and the RhodaLED (Biofrontera) light sources. FIG. 3B shows protoporphyrin IX (PpIX)-weighted spectrum showing wide variation in effective irradiance.

FIGS. 4A, 4B, 4C and 4D illustrate representations of Monte Carlo simulations. FIG. 4A illustrates a geometry used for Monte Carlo simulations (FIG. 4A). Tissue optical properties $\mu_s$ (FIG. 4B) and $\mu_a$ (FIG. 4C) were defined between 350 nm and 900 nm for each of the 7 tissue layers. A constant refractive index (n) and anisotropy (g) were assumed for each layer and are provided in FIG. 4D, but these values could also be defined by wavelength.

FIG. 5A illustrates fluence rate at various depths in a 7-layer tissue model, based on a simulated spectrally uniform light source.

FIG. 5B illustrates the PpIX-weighted effective fluence rate in the same model of FIG. 5A.

FIG. 5C illustrates geometry of a 7-layer skin model, where arrows indicate depths used in FIG. 5A and FIG. 5B.

DETAILED DESCRIPTION

Figure 1:
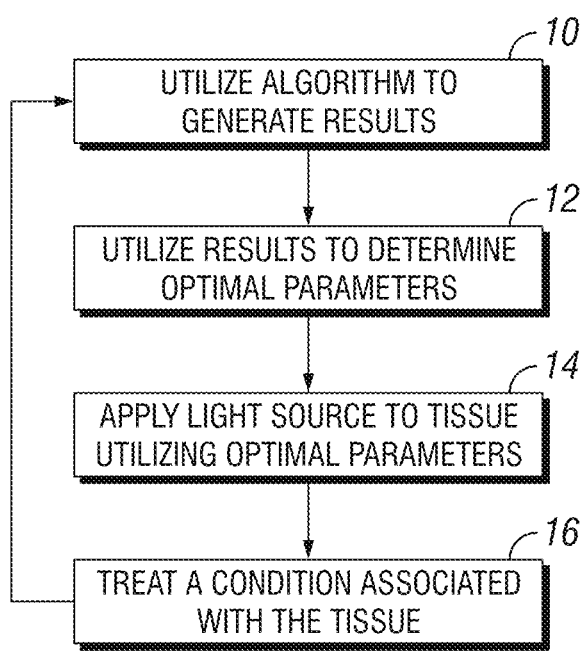
FIG. 1 depicts a method of determining optimal parameters for application of light from a light source to apply to a tissue according to an aspect of the present disclosure.
Figure 2F:
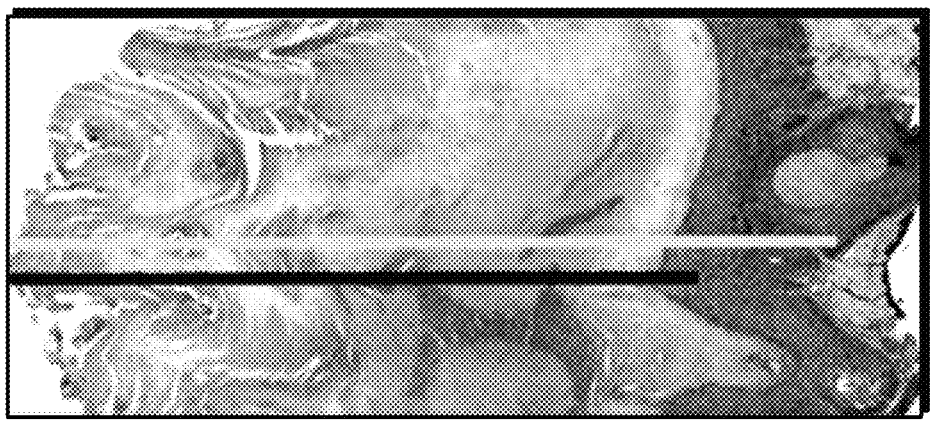
FIGS. 2A, 2B, 2C, 2D, 2E, and 2F illustrate representative skin lesions. The black line represents the distance from the surface of the corneal layer to the surface of the lesion. The yellow line represents the distance from the surface of the corneal layer to the base of the lesion. An example of an actinic keratosis (FIG. 2A), basal cell carcinoma, superficial type (FIG. 2B), squamous cell carcinoma in situ (FIG. 2C), basal cell carcinoma, nodular type (FIG. 2D), invasive well-differentiated squamous cell carcinoma (FIG. 2E), and a hypertrophic actinic keratosis (FIG. 2F) are shown.
Figure 2E:
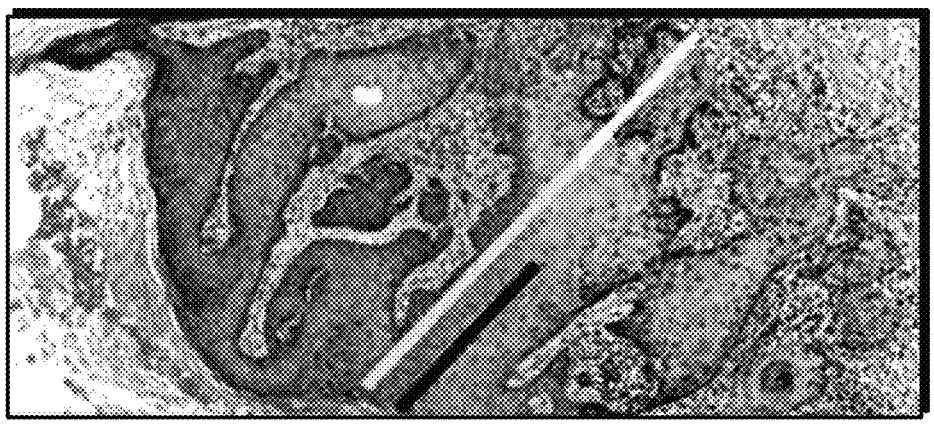
Figure 2B:
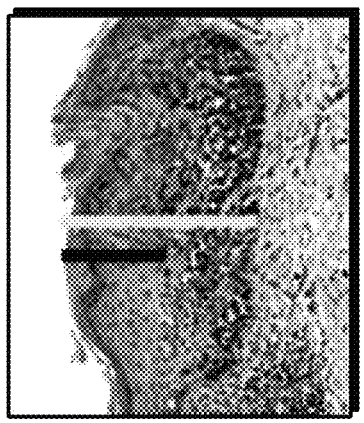
Figure 2D:
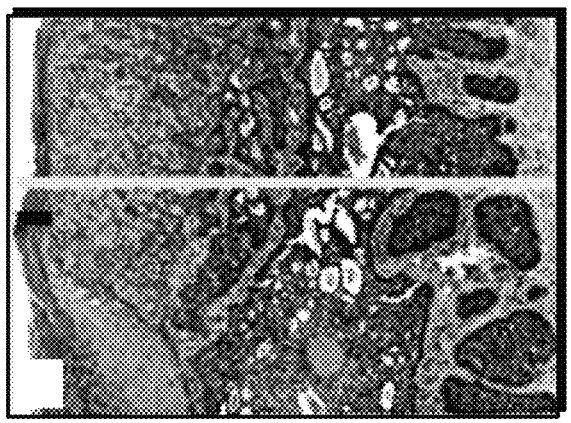
Figure 2A:
Figure 2C:
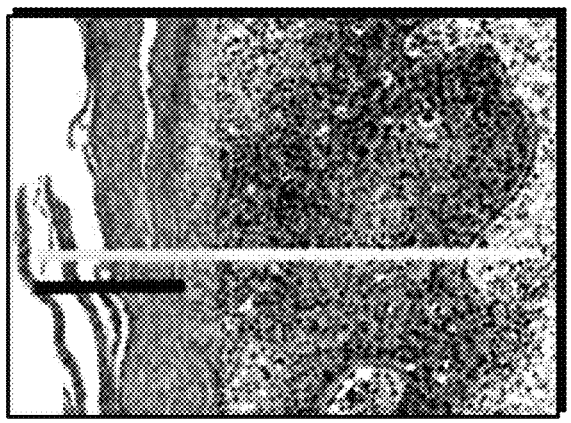

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that include more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Using daylight as an activation mechanism for photodynamic therapy (PDT) of skin has been investigated over the past decade, and is now widely accepted in several countries, as a less painful and equally effective treatment mechanism when compared to conventional red or blue light activation. However, seasonal daylight availability and transient weather conditions complicate light dose estimations, especially in northern latitudes. Clinically, appropriate treatment months are identified based on latitude and season, and patients are treated for approximately 2 hours where appropriate sunlight is expected. Yet, the changes in solar irradiance due to the time of day and transient weather conditions confound reproducibility. Daylight PDT and similar low-fluence rate activation methods have been reported to be less painful than conventional PDT. Additionally, the ability to treat multiple patients simultaneously has economic benefits in certain healthcare systems.

While lights used in conventional treatments are regulated medical devices that have well-characterized narrowband spectra and fluence rates, daylight is broad spectrum and the fluence rate changes on a continuous basis. Despite these well-known fluctuations, daylight PDT is an approved treatment in many countries without explicit guidance on dealing with daily weather prediction.

While reasonable approaches to delivering daylight PDT are always implemented, a more formalized approach to estimating light potential is warranted, as typical methods for dose planning place large burdens on clinical staff. A simple standardized method for estimating light dose during daylight-PDT could help improve inter-site reproducibility while minimizing treatment times.

In sum, a need exists for more effective methods for determining optimal parameters for the application of light from a light source into tissue. For instance, a need exists for more effective methods of determining optimal parameters for the application of daylight into skin by considering numerous factors, such as skin tone and daylight incubation times. Various embodiments of the present disclosure address the aforementioned need.

In some embodiments, the present disclosure pertains to methods of determining optimal parameters for application of light from a light source to a tissue. In some embodiments illustrated in FIG. 1, the methods of the present disclosure generally include one or more of the following steps of: utilizing an algorithm to generate results related to estimating light flow from the light source into the tissue (step 10); and utilizing the results to determine optimal parameters for applying the light source to the tissue (step 12). In some embodiments, the methods of the present disclosure also include a step of applying the light source to the tissue using the optimal parameters (step 14). In some embodiments, the application of the light is utilized to treat a condition associated with the tissue (step 16). In some embodiments, the method can be repeated until a desired therapeutic outcome is met or until more optimal parameters are achieved.

As set forth in more detail herein, the methods of the present disclosure can have numerous embodiments. For instance, the methods of the present disclosure can include various algorithms and methods for the generation of results relating to estimating light flow. In addition, the methods of the present disclosure can provide various generated results and optimal parameters related to the estimated light flow. Furthermore, the methods disclosed herein may utilize various light sources on a variety of tissues for different applications. In addition, the methods of the present disclosure may have various advantageous properties. As such, the methods of the present disclosure can provide for numerous applications, such as, but not limited to, therapeutic applications (e.g., daylight photodynamic therapy).

Algorithms

As set forth in more detail herein, the methods of the present disclosure can include various types of algorithms. For instance, in some embodiments, the algorithms can be models. In some embodiments, the algorithms include, without limitation, a Monte Carlo model, a broad-spectrum light fluence model, a Monte Carlo model of broad-spectrum light fluence, optical radiative transport models, optical diffusion models, and combinations thereof.

In some embodiments, the algorithms can include a seven-layer skin model. In some embodiments, the seven-layer skin model can include, without limitation, stratum corneum layers, living epidermis layers, papillary dermis layers, upper blood net dermis layers, reticular dermis layers, deep blood dermis layers, subcutaneous fat layers, and combinations thereof. In some embodiments, the algorithm is a location informed model.

In some embodiments, the algorithm utilizes at least one factor to estimate light flow. In some embodiments, the factor can include, without limitation, type of the light source, position of the light source, light fluence from the light source, location specific information, models of diffusion kinetics and spectral absorption characteristics of a photosensitive compound of interest, melanin content of the tissue, thickness of the tissue, thickness of a lesion on the tissue, pigmentation, actinic keratosis thickness, spectrally-resolve attenuation introduced by topical applications to tissue (e.g., sunscreen), and combinations thereof.

In some embodiments, the factor includes location specific information. In some embodiments, the location specific information includes, without limitation, weather forecasts, cloud coverage, ultra-violet (UV) index, elevation, temperature, barometric pressure, atmospheric pressure, chance of precipitation, humidity, relative humidity, wind speed, wind direction, air quality, average air particulate size, spectrally-resolve attenuation introduced by physical barriers (e.g., glass or plastic), and combinations thereof.

In some embodiments, data pertaining to the algorithms are stored in a remotely accessible or centralized database. As such, the data pertaining to the algorithms can be updated for example, for continual improvement, such as, but not limited to, improvements to the data, improvements to models, to provide revisions to existing data, to provide revisions to existing models, and combinations thereof.

In more specific embodiments, the factor includes spectrally-resolve attenuation introduced by physical barriers (e.g., glass or plastic). In some embodiments, the factor is applicable when glass or windows shift a transmission spectra. In such embodiments, the algorithms of the present disclosure would register the degree of attenuation for the site during the site assessment. In some embodiments, such information is stored in a central database.

Generation of Results

As set forth in more detail herein, the methods of the present disclosure can utilize algorithms to generate various types of results. For instance, in some embodiments, at least a portion of the results are generated via at least one method that includes, without limitation, estimating effective fluence rates, comparing the fluence rates between multiple broadband and narrowband sources, estimating effective fluence rates for multi-layer tissue models of varying geometry and optical properties, analyzing production of a photosensitive compound, analyzing photobleaching of a photosensitive compound, generating an effective total fluence for various treatment times, determining a dynamic dose range, and combinations thereof.

In some embodiments, the methods of the present disclosure can utilize algorithms to generate results related to estimating effective fluence rates for multi-layer tissue models of varying geometry and optical properties. In some embodiments, the algorithms take into account a change in geometry or optical properties of a multi-layer tissue model. For instance, different body sites and age can impact multi-layer tissue thickness. Similarly, melanin content can alter the optical properties of superficial layers.

In some embodiments, at least a portion of the results are generated via at least estimating effective fluence rates. In some embodiments, the estimating effective fluence rates includes utilizing tissue optical properties. In some embodiments, the tissue optical properties include at least one property. In some embodiments, the property can include, without limitation, refraction, polarization, reflection, absorption, photoluminescence, transmittance, diffraction, dispersion, dichroism, scattering, anisotropy, birefringence, color, photosensitivity, optical properties attributed to melanin, and combinations thereof.

In some embodiments, the tissue optical properties can be modified for varying skin types. In some embodiments, the tissue optical properties can be modified for varying skin pigmentations. In some embodiments, the tissue optical properties can be modified for varying disease types. In some embodiments, the tissue optical properties can be modified for various stages of a disease. In some embodiments, the disease is acne. In some embodiments, the disease is cancer. In some embodiments, the stage of the disease is pre-cancer.

In some embodiments, at least a portion of the results are generated via comparing the fluence rates between multiple broadband and narrowband sources. In some embodiments, the comparing the fluence rates between multiple broadband and narrowband sources utilizes data that can include, without limitation, narrowband sources modeled based on clinically available sources, broadband sources based on measurements taken by a spectroradiometer, measured narrowband sources, measured broadband sources, and combinations thereof.

In some embodiments, at least a portion of the results are generated via analyzing production and photobleaching of a photosensitive compound. In some embodiments, the photosensitive compound is protoporphyrin IX (PpIX).

In some embodiments, the spectral absorption of the photosensitive compound are used to estimate activation. In some embodiments, the activation can be related to models of spectral absorption, fluence rate, local oxygen availability, and photobleaching.

In some embodiments, the PpIX concentration does not impact the tissue optical properties, and as such, the estimating effective fluence rates are not based on PpIX absorption. In some embodiments, the PpIX concentration impacts the tissue optical properties, and as such, the estimating effective fluence rates are at least partially based on PpIX absorption.

In some embodiments, the analyzing production and photobleaching of the photosensitive compound utilizes data that can include, without limitation, diffusion rate of a prodrug, diffusion rate of a drug, rate and efficiency that a prodrug is converted to the photosensitive compound, rate and efficiency that a drug is converted to the photosensitive compound, estimated photobleaching data, and combinations thereof. In some embodiments, the estimated photobleaching data includes, without limitation, an initial photosensitive compound concentration, fluence rate, a photosensitive compound weighted effective fluence rate, a photobleaching constant, and combinations thereof.

In some embodiments, at least a portion of the results are generated via generating an effective total fluence for various treatment times. In some embodiments, the generating the effective total fluence for various treatment times includes, without limitation, identifying a treatment time, incubation time based on an initial depth distribution of a photosensitive compound, and combinations thereof. In some embodiments, the generating the effective total fluence for various treatment times depends, at least in part, on at least one of a spectrum and fluence rate of the light.

In some embodiments, at least a portion of the results are generated via determining a dynamic dose range. In some embodiments, the dynamic dose range is determined from data that can include, without limitation, initial incubation times, estimated ignition incubation times, surface irradiation values, estimated irradiation values, a range of surface irradiation values, an estimated range of surface irradiation values, and combinations thereof.

In some embodiments, the dynamic dose range is determined from a light source fluence rate at depths in the tissue that are linearly scaled to represent a range of surface irradiation values. In some embodiments, the determining the dynamic dose range includes identifying an effective photodynamic dose. In some embodiments, the effective photodynamic dose is defined as a product of threshold effective fluence and photosensitive compound concentration.

As set forth in more detail herein, the methods of the present disclosure can include generated results related to estimating light flow from the light source into the tissue. For instance, in some embodiments, the results can include, without limitation, light flow into the tissue, a photodynamic dose for a photosensitive compound at depths into the tissue, sunlight available at depths into the tissue, treatment dose for a photosensitive compound, minimum time needed to reach a threshold photodynamic dose, and combinations thereof.

In some embodiments, the results include a chart to prescribe minimal treatment times to achieve depth-dependent cytotoxic effect based on incubation times and irradiance values for a plurality of light sources. In some embodiments, the chart provides an estimate of depth of potential photosensitive compound activation as a function of treatment time for each light source of the plurality of light sources. In some embodiments, the chart includes clinically relevant dose planning information used to define treatment times required to achieve activation at specific depths for each light source of the plurality of light sources over a range of irradiance values and photosensitive compound incubation times. In some embodiments, the chart includes data that can include, without limitation, indications of seasons most commonly associated with given irradiance for various latitudes, lesion type, estimated depth, melanin content, photosensitive compound production rate, and combinations thereof.

Additionally, in some embodiments, the chart can include, without limitation, lookup values of light flow into a tissue, photodynamic dose for a photosensitive compound at depths into a tissue, sunlight available at depths into skin, best treatment dose for photosensitive compounds, minimum time needed to reach a threshold photodynamic dose, the generated results, the determined optimal parameters (as described in further detail herein), and combinations thereof.

In some embodiments, the chart can be further modified to include factors such as, but not limited to, lesion type, estimated depth, melanin content, a photosensitive compound (e.g., PpIX) production rate, and combinations thereof. In some embodiments, the chart can be included in a web-based application. In some embodiments, the chart can be included in a phone-based application. In some embodiments, the chart can be further automated in a tool used to measure spectral irradiance. In some embodiments the chart can be used with feedback collected from photosensitizer concentration estimates. In some embodiments, the chart can be in a form including, but not limited to, a lookup table, a database, a centralized database, and combinations thereof.

Determining Optimal Parameters

Additionally, as set forth in more detail herein, the methods of the present disclosure can utilize generated results to determine optimal parameters for applying a light source to a tissue. For instance, in some embodiments, the optimal parameters can include, without limitation, a light source type, a dosage, a minimum treatment time, a maximum treatment time, a recommended exposure time, daylight hours for optimal treatment, sunlight hours for optimal treatment, location for optimal sunlight exposure, location for optimal daylight exposure, light flow into the tissue, effective fluence rates for the tissue, a total treatment time based on a correlation of the light flow into the tissue and the effective fluence rates, feedback mechanisms based on measurements of photosensitizer production and photobleaching, and combinations thereof.

In some embodiments, the determined optimal parameters include one or more of the following: (1) light flow into the tissue; (2) effective fluence rates for the tissue; (3) a total treatment time based on a correlation of the light flow into the tissue and the effective fluence rates; and (4) combinations thereof.

Application of Light Sources

As set forth in further detail herein, the methods of the present disclosure can apply various light sources to tissues. For instance, in some embodiments, the light source can include, without limitation, daylight, sunlight, simulated light, simulated daylight, simulated sunlight, naturally generated light, artificially generated light, natural light generated by the sun, artificial light generated by a halogen light, a compact fluorescent lamp light, a light emitting diode (LED) light, a blue LED light, a red LED light, a white light, or a lamp light, broad-spectrum light, narrow-spectrum light, broadband light, narrowband light, and combinations thereof.

Tissues

In addition, the methods of the present disclosure can be utilized for the application of light sources to various types of tissue. For instance, in some embodiments, the tissue is skin tissue. In some embodiments, the skin tissue includes, without limitation a tumor site, non-melanoma skin cancer, a lesion site, actinic keratosis, hypertrophic actinic keratosis, squamous cell carcinoma, invasive squamous cell carcinoma, basal cell carcinoma (superficial type), basal cell carcinoma (nodular type), acne vulgaris, rhinophyma, wrinkles, sun-damage, and combinations thereof.

In some embodiments, the skin includes various layers. In some embodiments, the layers can include, without limitation, a stratum corneum layer, a living epidermis layer, a papillary dermis layer, an upper blood net dermis layer, a reticular dermis layer, a deep blood dermis layer, a subcutaneous fat layer, or combinations thereof.

Treatment of Conditions

In some embodiments, the application of light from a light source to a tissue can be utilized to treat various conditions associated with various tissues. For instance, in some embodiments, the methods of the present disclosure can be utilized to treat a condition associated with the skin. In some embodiments, the condition can include, without limitation, a skin tumor, non-melanoma skin cancer, a lesion, actinic keratosis, hypertrophic actinic keratosis, squamous cell carcinoma, invasive squamous cell carcinoma, basal cell carcinoma (superficial type), basal cell carcinoma (nodular type), cancer, acne vulgaris, rhinophyma, wrinkles, sun-damage, and combinations thereof.

The methods of the present disclosure can be utilized for various therapeutic uses. For instance, in some embodiments, the methods of the present disclosure can further include applying the light source to the tissue using the optimal parameters. In some embodiments, the application of the light source occurs in the presence of a photosensitive compound. In some embodiments, the photosensitive compound is protoporphyrin IX (PpIX).

In some embodiments, the methods of the present disclosure include application of daylight photodynamic therapy (DPDT) to the skin. In some embodiments, DPDT is utilized to treat a condition associated with the skin.

In some embodiments, depending on the spectrum and fluence rate of the treatment light, the distribution of a photosensitive compound (e.g., PpIX) can dynamically change during treatment. In some embodiments, depending on the duration of light treatment, the photosensitive compound distribution can remain the same during treatment.

Applications and Advantages

The present disclosure can have various advantages. For instance, in some embodiments, the methods of the present disclosure have at least the following valuable features: (1) a onetime site assessment to provide initial parameters; (2) models and algorithms can be continually updated with data pertaining to the models or algorithms to ensure the most accurate parameters are generated; (3) the methods utilize algorithms that consider various factors; (4) the methods presented herein eliminate burdensome tasks for clinicians; (5) the methods presented herein can easily be adapted to mobile devices, web interfaces, and other electronic devices; and (6) quick determination of optimal parameters (e.g., light flow into a tissue, effective fluence rates for the tissue, and a total treatment time based on a correlation of the light flow into the tissue and the effective fluence rates).

As such, the methods of the present disclosure can be utilized in various manners and for various purposes. For instance, in some embodiments, the algorithms of the present disclosure can be utilized to prescribe minimal treatment times to achieve depth-dependent cytotoxic effect based on incubation times and irradiance values for each light source, thereby providing optimal photodynamic therapy to a subject.

In some embodiments, the methods of the present disclosure can be utilized in daylight-based photodynamic therapy of skin. Daylight-based photodynamic therapy of skin is becoming more common for the treatment of actinic keratosis and non-melanoma skin cancers. While light doses used in conventional photodynamic therapy with narrow-band light, such as blue or red light, are well defined, daylight-photodynamic therapy is much less controlled. There are many variables that need to be considered to determine the delivered light doses. As such, dose-planning tools utilizing the algorithms of the present disclosure are useful to reduce burdens placed on clinicians.

In some embodiments, the algorithms of the present disclosure can be utilized to accommodate light-based treatments based on seasonal sunlight variations. While models of seasonal sunlight variation have been proposed as a way to estimate sufficient light availability, transient weather patterns confound these methods. Using existing global positioning system (GPS) information from a common mobile device allows systems to query real-time weather information. This weather information can then be used to update seasonal models of sunlight availability. The real-time feedback can be used to update treatment duration with minimal effort needed by the clinician.

In some embodiments, the algorithms of the present disclosure can also be utilized to provide estimates of light fluence and photodynamic doses at depths into various tissues. While even in more controlled conventional photodynamic therapy, only surface light dose is considered, differences in skin lesion thickness can indicate a needed change in the conventional light treatment strategy. As such, the algorithm-based methods of the present disclosure help clinicians refine conventional treatments to account for lesion thickness.

In some embodiments, the algorithms of the present disclosure can be continually improved and revised. For instance, in some embodiments, multiple algorithms of the present disclosure can be run and stored in a centralized database. In some embodiments, the centralized database can be accessed remotely. This allows for continued improvements and revisions to existing algorithms and data pertaining to the algorithms of the present disclosure. Parameters such as, but not limited to, melanin content, lesion thickness, and light source, can be customized and the results stored for later retrieval.

Unlike traditional photodynamic therapy applications, in some embodiments, the algorithms of the present disclosure can be used for estimating sunlight available at depths into skin to activate photosensitive compounds, such as those used in photodynamic therapy, based on location-specific weather forecasts. In some embodiments. Monte Carlo models of broad-spectrum light fluence in skin tissue can be utilized to generate results, optimal parameters, charts, or lookup tables of light fluence and photodynamic dose at depths into tissue, which can be stored in a remotely accessible database.

In some embodiments, a location-aware mobile device can access this database and also retrieve local weather information to estimate potential light fluence at depths into tissue. In some embodiments, site assessments can be performed to identify related information that can include, but is not limited to, fixed objects that create hard shadows at predicable times of the day throughout the year. In some embodiments, the related information can be collected as a one-time measurement for the site. In some embodiments, the one-time measurement can be used with changing weather forecasts to provide guidance on long-term and short-term treatment schedules.

For example, in the winter, a long-term schedule identified by the algorithms of the present disclosure may indicate that there is only a three hour block available without sunlight being obstructed. On the other hand, the same location may indicate six hours of sunlight during summer months.

In some embodiments, these assessments can be utilized with the algorithms of the present disclosure to create a scheduling system linking relevant information to a shared calendar for treatment planning. In some embodiments, the treatment planning can allow for follow-up appointments planning many months in advance, that only need to be confirmed when a weather forecast is available.

In some embodiments, databases can include models of diffusion kinetics and spectral absorption characteristics of photosensitive compounds which can be combined with the light fluence estimates to determine photodynamic doses. In some embodiments, mobile devices can use the models in the database, combined with location-specific data, for example, but not limited to, weather information, to provide an estimate of the minimum time needed to reach threshold photodynamic doses. In some embodiments, the algorithms of the present disclosure can be extended to include common disease morphologies, melanin contents, and various photosensitive compound production rates (e.g., PpIX production rates).

Previous methods have utilized a combination of seasonal fluctuations, luminance measurements, and latitude as a metrics for light availability. Daily and near real-time weather fluctuations have not been considered for daylight photosensitizer activation or treatment planning. Location-aware mobile devices provide the ability to estimate daylight irradiance in near real-time. While luminance measurements can be correlated with solar irradiation, they are not easily used in conjunction with alternate light sources or in the presence of attenuating materials such as glass or sunscreen. While other methods may consider surface tissue irradiance, the models of the present disclosure account for multiple layers of tissue, providing dose estimates at depth. The depth-based dose estimates can then be used to account for tissue pigmentation or lesion morphology to provide more accurate dose estimations.

ADDITIONAL EMBODIMENTS

Reference will now be made to more specific embodiments of the present disclosure and experimental results that provide support for such embodiments. However, Applicants note that the disclosure below is for illustrative purposes only and is not intended to limit the scope of the claimed subject matter in any way.

Example 1. Modeling Protoporphyrin IX (PpIX) Effective Light Fluence at Depths into the Skin for Photodynamic Therapy (PDT) Dose Comparison This Example describes modeling protoporphyrin IX (PpIX) effective light fluence at depths into the skin for photodynamic therapy (PDT) dose comparison.

Daylight-activated photodynamic therapy (PDT) has seen increased support in recent years as a treatment method for actinic keratosis and other non-melanoma skin cancers. The variability observed in broad-spectrum light used in this methodology makes it difficult to plan and monitor light dose, or compare to lamp light doses. This Example expands on the commonly used protoporphyrin IX (PpIX)-weighted effective surface irradiance metric by introducing a Monte Carlo method for estimating effective fluence rates into depths of the skin. The fluence rates are compared between multiple broadband and narrowband sources that have been reported in previous studies, and an effective total fluence for various treatment times is reported. A dynamic estimate of PpIX concentration produced during pro-drug incubation and treatment is used with the fluence estimates to calculate a photodynamic dose. Even when there is up to a 5× reduction between the effective surface irradiance of the broadband light sources, the effective fluence below 250 μm depth is predicted to be relatively equivalent. An effective threshold fluence value (0.70 $J_{eff}/cm^2$) is introduced based on a meta-analysis of previously published aminolevulinic acid (ALA)-PpIX induced cell death. This was combined with a threshold PpIX concentration (50 nM) to define a threshold photodynamic dose of 0.035 u M $J_{eff}/cm^2$. The threshold was used to generate lookup tables to prescribe minimal treatment times to achieve depth-dependent cytotoxic effect based on incubation times and irradiance values for each light source.

Example 1.1. Introduction

Photodynamic therapy (PDT) for treatment of actinic keratosis (AK) and other non-melanoma skin cancers has been an approved clinical practice for decades, and just in the past few years daylight-activated PDT for AK has gained support as an approved treatment method. With the shift from conventional PDT use of blue (415 nm) or red (633 nm) lamp sources, to daylight-PDT, where broadband sources like the sun or other artificial white lights have been explored, the complexity of light dose estimation is increased.

Prescribing a sufficient photodynamic dose requires knowledge of both how light interacts with tissue as well as how the clinical presentation can influence the tissue morphology. As clinical context for the current Example, FIG. 2 shows histopathology examples of actinic keratosis (AK) and other non-melanoma skin cancers, where Table 1 provides the corresponding depth profile of each lesion. From these case examples it can be observed there is a range over which the photodynamic dose must be effective, and this dose will vary based on both PpIX production and light fluence reaching the entirety of the lesion. Yet, most treatments only consider the light dose at the skin surface.

While there have been proposed methods to estimate the spectrally-weighted light dose relative to the PpIX spectrum, these approaches do not account for the spectral attenuation in the skin. Using Monte Carlo modeling, this Example aims to provide clinically relevant methods to understand how surface irradiance measurements can be used to estimate the light fluence rate at depth in tissue, which should allow informed decisions about treatment time and appropriate light sources, thus improving the ability to tailor PDT treatments based on the clinical presentation of the disease.

TABLE 1

Depths of Representative Skin lesions from FIG. 2.

| | Measurement from surface of corneal layer to surface of lesion (μm) | Measurement from surface of corneal layer to base of lesion (μm) |
|---|---|---|
| (A) Actinic keratosis | 189 | 222 |
| (B) Hypertrophic actinic keratosis | 1419 | 1708 |
| (C) Squamous cell carcinoma in situ | 305 | 1038 |
| (D) Invasive squamous cell carcinoma | 287 | 692 |
| (E) Basal cell carcinoma, superficial type | 214 | 403 |
| (F) Basil cell carcinoma, nodular type | 70 | 1108 |

In Europe, Metvix or MAL is the common form of ALA used for topical PDT, whereas Levulan is used in the United States. More recently, Ameluz has been approved in both markets for treatment of AK and tissue debridement. MAL-equivalent Luxerm and Ameluz are also approved in Europe for daylight-PDT. For conventional lamp activated PDT, all formulations are applied and let to incubate for a period on the order of hours and then activated with a blue (415 nm 10-25 $J/cm^2$) or red (633 nm, 37-125 $J/cm^2$) light. But, in the daylight PDT protocol, this can differ slightly depending on the drug formulation, but generally the incubation is minimized to be near 30 min and the activation solar irradiance is much lower. In conventional PDT, the PpIX production has been reported to penetrate up to depths of 2 mm with 3 h incubation, whereas during daylight-PDT PpIX is thought to be produced continuously during the treatment and few reports on depth are known. The shorter ALA incubation time combined with the lower irradiance and longer PpIX activation time is thought to be the driving factor in reports of lower pain with daylight PDT.

The spectral characteristics of light dictate the depth of potential PpIX activation. Due to tissue optical properties blue light will have a much more superficial activation profile than red light. However, PpIX has peak absorption in the blue (~410 nm), but also in Q-bands at 505 nm, 540 nm, 580 nm and 635 nm. Optimizing these factors, depth of activation and peak absorption, can be easily accomplished with narrowband light sources such as LEDs by altering the irradiance.

Figure 3A:
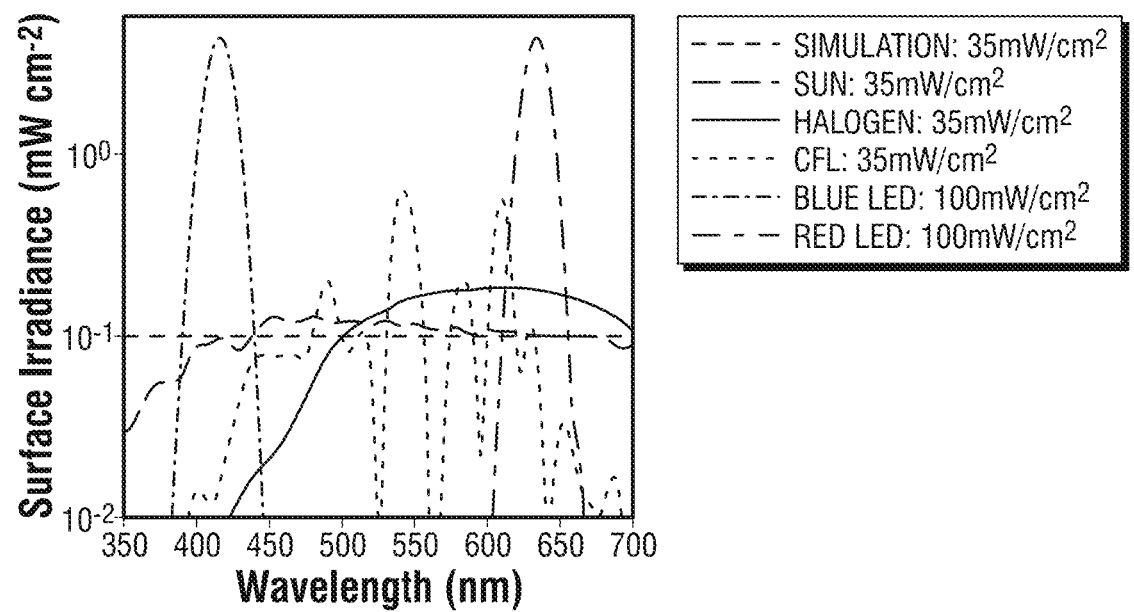
FIGS. 3A and 3B illustrate spectrum of six light sources.
Figure 3B:
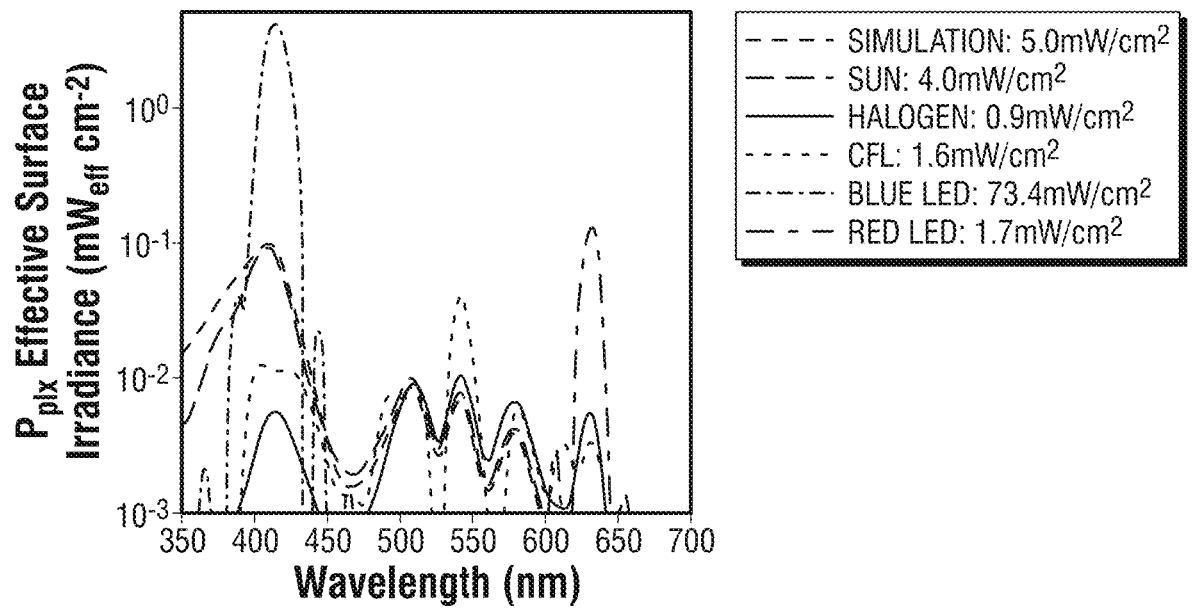

This optimization becomes slightly more challenging when broad-spectrum light sources are used, especially when using a natural light source such as the sun. The consensus method for comparing broad-spectrum light sources is to weight the measured spectrum by the normalized PpIX spectrum resulting in a measure of effective irradiance. Briefly, this is accomplished by first measuring the spectrally resolved irradiance at the skin surface (FIG. 3A). This spectrum is then multiplied by a normalized PpIX absorption spectrum, resulting in a measure of effective irradiance (FIG. 3B). The effective irradiance provides a weighting factor for the probability of PpIX activation so that different light sources can be more easily compared. However, in the presence of tissue attenuation, the light fluence rate will vary drastically as a function of both wavelength and depth.

Previous Monte Carlo studies have investigated the interactions of light, tissue and PpIX from a variety of perspectives. Comparisons of clinical fluorescence measurements with tissue models have been used to estimate the depth distribution of PpIX. Expanding on this idea, a model using three excitation sources was developed to study the oxygen concentration and resulting reactive oxygen caused by PpIX activation. A similar study was conducted which modeled both daylight and red-light activation of PpIX for a skin tumor model, and in subsequent work modeled the continuous production of PpIX during both conventional and daylight-PDT treatment. This Example expands on previous studies by using a 7-layer skin model with the ability to Monte Carlo model any light source in the 350-900 nm spectral range at 10 nm spectral resolution. The resulting light fluence information is then combined with estimates of PpIX production and photobleaching as well as light fluence thresholds to tabulate clinically-relevant treatment times based upon the applied light source and the desired depth of activation in tissue.

A simplified model to determine the potential for PpIX activation may consider only light fluence in tissue, which assumes a sufficient and uniform distribution of PpIX. However, recent models have shown the importance of accounting for PpIX distribution when determining the photodynamic dose. As such, estimates of PpIX distribution have been considered using both incubation times of 30 min or less, commonly used in daylight-PDT protocols, and incubation times of over an hour which better represent conventional-PDT. Since the irradiance used in these protocols cover a wide range, photobleaching will occur over differing time-scales. The present model assumes oxygen concentration remains sufficient throughout the treatment period.

Example 1.2. Monte Carlo Model

Using the Monte Carlo software GAMOS, a 7-layer skin model (FIG. 4 and FIG. 5) was defined based on previous studies. Tissue optical properties ($\mu_a$, $\mu_s$, g, n) were defined between 350 nm-900 nm at a 10 nm spectral spacing (FIG. 4) using the tissue-optics plugin for GAMOS. The tissue optical properties assume lightly pigmented skin, which correspond to approximately 1% melanin in the epidermis (skin layer 2 in FIG. 4). A custom Python script converted the input file into a baseline template for a GAMOS geometry file. The total tissue volume was placed in a 20 cm×20 cm×2 cm box where the top 7.9 mm contained the explicitly defined skin model. A voxelized parallel geometry was defined with 1 cm×1 cm×10 µm voxels within the skin to measure the fluence. A 5 cm diameter disc-shaped light with 1° divergence was modeled as the source 60 mm above the skin surface. The voxelized geometry is only defined as a single XY volume per 10 um Z-step to reduce the analysis complexity. The overall XY dimensions of the tissue volume are much larger than the voxelized geometry to better simulate a semi-infinite slab geometry. PpIX absorption is not considered in the current model, since it is assumed the concentration would not be large enough to have a substantial impact on the overall tissue optical properties. Simulations were run using $10^7$ photons for each of the defined wavelengths.

The simulations were run using Amazon Web Services (AWS) Batch service. Briefly, a simulation template was created and uploaded to an AWS S3 bucket. This template contained a zip file with the necessary input files and a bash script that processed simulation input arguments (source wavelength, number of photons, and random seed). An AWS Batch job definition was generated programmatically, which specified compute parameters for each simulation job (1-3 virtual CPUS, and 2000-4000 MB memory). The jobs were then added to the queue and run in parallel using AWS EC2 instances (c4.large-c4.8xlarge). Simulation outputs were stored in sub-directories of the S3 Bucket and retrieved using the AWS command line interface for analysis on a local computer. All analysis was done using custom Python scripts.

Example 1.3. Light Fluence

The following sections compare narrowband blue and red light at clinically relevant surface irradiance with broadband sources that have been reported in previous daylight and low-fluence-rate PDT models. The narrow-band sources are modeled based on clinically available sources, such as the Blue-U (Sun/DUSA) and the RhodaLED (Biofrontera). The broadband sources are based on measurements taken by a spectroradiometer (Apogee SS-110).

Like the PpIX effective surface irradiance, the effective fluence rate was calculated by weighting the fluence rate by the PpIX absorption spectrum. Using the PpIX-weighted effective fluence rate at various depths in tissue, the effective light dose could then be determined for each source.

In broad-spectrum PDT applications, the effective light dose is often reported as a product of the normalized PpIX absorption spectrum and the source spectrum. This idea was applied to the fluence rate estimates by first taking the idealized case where each modeled wavelength had the same number of photons ($10^7$), and then extended to match measured light sources by first weighting the model by the measured spectrum (1) and then applying the PpIX absorption weighting (2). The estimated spectral fluence rate at depth z, was:

$$\emptyset(\lambda,z) \text{ (mW/cm}^2) = E_{meas}(\lambda,0) * \emptyset_{model}(\lambda,z) \quad (1)$$

where $E_{meas}$, is the spectrally measured irradiance at the surface and $\varphi_{model}$ is the spectral attenuation due to tissue as modeled for the defined wavelength ($\lambda$) at depth z.

Then the effective spectral fluence rate was calculated as:

$$\varphi_{eff}(\lambda,z) \text{ (mW}_{eff}/\text{cm}^2) = E_{meas}(\lambda,0) * \emptyset_{model}(\lambda,z) * A_{PpIX}(\lambda) \quad (2)$$

where $A_{PpIX}$ is the normalized spectral attenuation of PpIX.

The effective fluence is the product of the effective fluence rate and the treatment time. The effective threshold fluence is based on previously reported fluence values for studies using at least 0.6 mM ALA and a laser or LED light source (Table 2). Since the wavelength for each study was reported for each cytotoxic probability distribution with mean fluence ($D_P$) and full-width half maximum (FWHM) of the distribution ($\Delta D$), the equivalent effective fluence could then be calculated using the PpIX absorption spectrum weighting (3-5).

$$\zeta_\lambda = \int_{\mu-3\sigma}^{\mu+3\sigma} A_{PpIX}(\lambda)d\lambda \quad (3)$$

$$D_{P,eff} = \zeta_\lambda D_P \text{ and } \sigma_{D,eff} = \zeta_\lambda \sigma_D \quad (4)$$

$$\sigma_{D,eff,pooled} = \sqrt{\frac{\Sigma \sigma_{D,n}}{N}} \quad (5)$$

where $A_{PpIX}$ is again the normalized spectral attenuation of PpIX over the wavelength range of interest and $\sigma_\theta$ is the standard deviation calculated from the probability distribution $\Delta D$.

Example 1.4. PpIX Production and Photobleaching

Since the Monte Carlo model only considers light fluence, and not PpIX production or photobleaching, Python scripts were developed to perform this portion of the analysis. PpIX production was estimated based on a previous model and the parameters used in this Examples match those. Briefly, the PpIX concentration is based on the diffusion rate of the pro-drug (6), and the rate and efficiency the drug is converted to PpIX (7).

The pro-drug concentration M is first calculated at depth z and time t using:

$$M(z,t) = M_0\left(1 - \text{erf}\left(\frac{z}{\sqrt{4Dt}}\right)\right) \quad (6)$$

where $M_0$ is the initial concentration of the pro-drug applied to the surface (z=0) at time t=0 and is assumed to be $6\times10^{16}$ cm$^{-3}$. D is the diffusion coefficient and assumed to be $6.9\times10^7$ cm$^2$ s$^{-1}$. The resulting PpIX production at depth z and time t can be calculated using:

$$P(z,t) = \frac{\varepsilon_p}{\tau_{ap}}\int_0^t e^{-\frac{t-t}{t_p}} M(z,t)dt \quad (7)$$

where $\varepsilon_p$ is the yield or proportion of pro-drug converted to PpIX, which is assumed to be 0.5, and $\tau_{ap}$ is the relaxation time or rate of conversion of the pro-drug and is assumed to be 8640 s. The rate of PpIX clearance is reflected in $\tau_p$ and is assumed to be 4680 s. The result of this calculation is the number of PpIX molecules per cubic centimeter. In this Example, this was converted to molar concentration to allow for better comparison with clinical findings.

Photobleaching was estimated as a simple exponential decay based on the initial PpIX concentration and fluence rate, but with two modifications:

$$C(z,t) = C_o(z)e^{-\emptyset_{eff}(z)t/\beta} \quad (8)$$

first, $\varphi_{eff}(z)$ is the PpIX-weighted effective fluence, and second, the photobleaching dose constant ($\beta$) is calculated for the peak PpIX absorption at 410 nm (0.65 J cm$^{-2}$) to determine the wavelength-dependent photobleaching dose constant, assuming $\beta$ (630 nm) to be 14 J cm$^{-2}$. $C_0(z)$ is the initial PpIX concentration at the specified depth, z.

PpIX concentrations resulting from different incubation periods, when light is assumed to be negligible, are first calculated using equations (6) and (7). Then, both PpIX production and photobleaching are considered during the light treatment phase. The PpIX concentration at depth is updated iteratively to account for both processes during treatment.

TABLE 2

Light dose distribution parameters used to calculate effective cytotoxic threshold.

| Wavelength (nm) | 405 | 405 | 514 | 514 | 630 | 634 |
| --- | --- | --- | --- | --- | --- | --- |
| $D_P/(\text{J/cm}^2)$ | 0.14 | 0.14 | 0.16 | 1.11 | 0.79 | 1.54 |
| $\sigma_\upsilon(\text{J}_{eff}/\text{cm}^2)$ | 0.13 | 0.13 | 0.09 | 0.24 | 0.27 | 1.49 |
| $D_{P,eff}(\text{J}_{eff}/\text{cm}^2)$ | 0.12 | 0.12 | 0.01 | 0.07 | 0.01 | 0.03 |
| $\sigma_{D,eff}(\text{J}_{eff}/\text{cm}^2)$ | 0.11 | 0.11 | 0.01 | 0.01 | 0.01 | 0.02 |

Example 1.5. Photodynamic Dose

Initial incubation times of 5, 30, 60, and 120 min were assumed. For each light source the fluence rate at depths in tissue was linearly scaled to represent a range of surface irradiance values. Through iteratively calculating the PpIX distribution based on these input parameters, the photodynamic dose can be determined over a range of times and resulting effective fluence values. An effective photodynamic dose is defined as the product of the threshold effective fluence and a PpIX concentration of 50 nM.

Example 1.6. Results

Figure 6A:
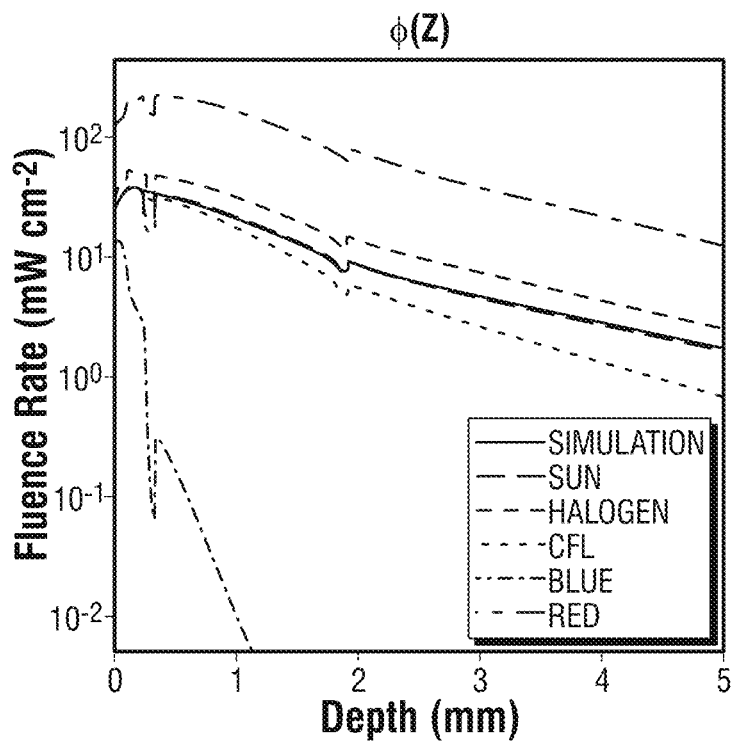
FIGS. 6A and 6B illustrate a comparison of the fluence rate (FIG. 6A) and effective fluence rate (FIG. 6B) as a function of depth for the uniform simulation, sun, compact fluorescent lamp (CFL), halogen, a blue light emitting diode (LED), and a red LED.
Figure 6B:
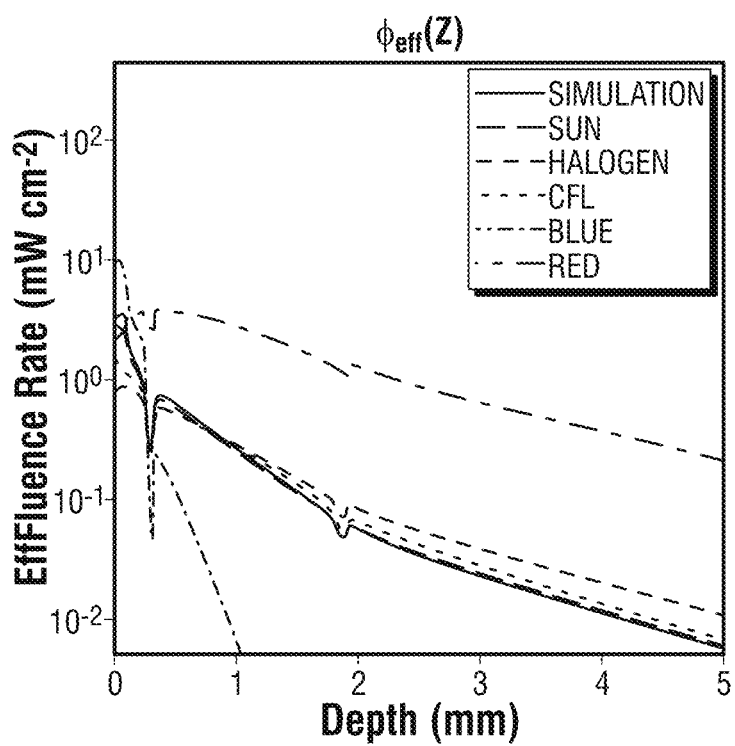

Using the normalized PpIX absorption spectrum as a weighting factor is common method to compare the effective irradiance of different broadband light sources. For the light sources considered in this Example, even though the broadband sources have an equal irradiance, the PpIX-effective irradiance demonstrates up to a 5× difference (FIG. 3). Similarly, the blue and red LED sources have respective effective fluence rates of just 73% and 2% of the unweighted values While PpIX-weighting improves the ability to compare surface irradiance, it does not consider tissue optical properties. FIG. 5A shows how the fluence rate of a spectrally uniform light source is attenuated by tissue, as simulated with the 7-layer skin model. Furthermore, when the normalized PpIX absorption is used as a weighting factor, the spectral characteristics of effective fluence rates are again modified (FIG. 5B). This fluence rate can be estimated for each light source at a spacing of the 10 μm voxels throughout the depth of the model by summing over the spectral range of interest (350 nm-700 nm). Similarly, the effective fluence rate can be calculated by considering the normalized PpIX absorption weighting factor. The results are the fluence rate and effective fluence rate as a function of depth, $\varphi(z)$ and $\varphi_{eff}(z)$, respectively (FIG. 6).

Figure 7A:
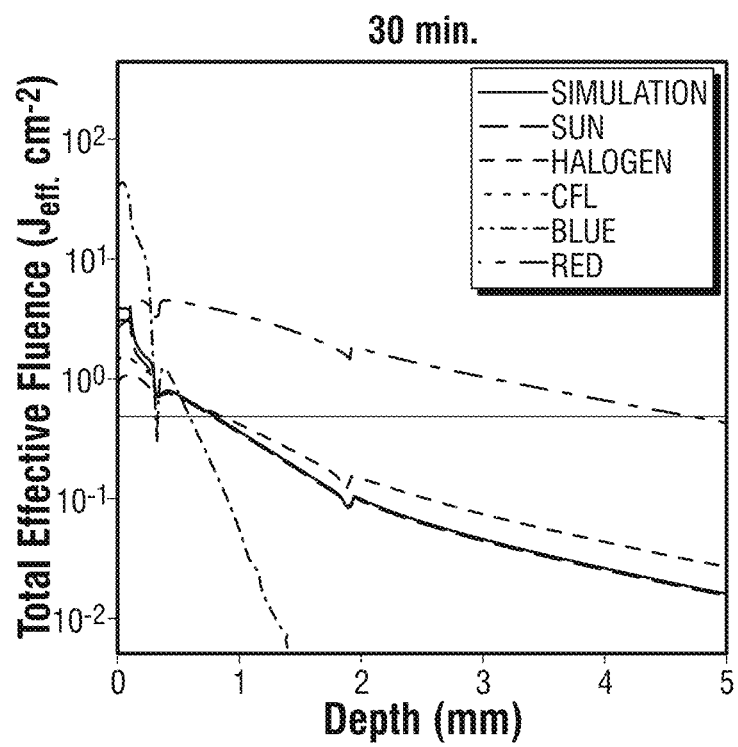
FIGS. 7A and 7B illustrate effective light fluence as a function of time and depth for two different treatment times showing how deeper light activation can be achieved by either extending treatment durations or using alternate light sources. The black line shows the expected threshold for PDT response at 0.7 $J_{eff}/cm^2$.
Figure 7B:
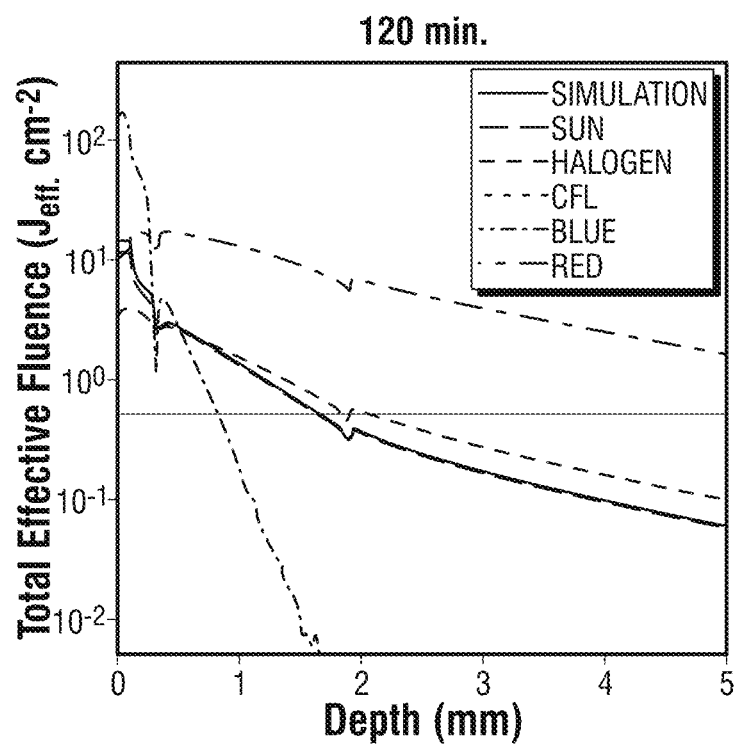

To determine an appropriate effective threshold fluence, a scalar value ($\zeta_\lambda$) was determined based on the reported central wavelength and assumed a 10 nm or 20 nm full-width half maximum (FWHM) distribution for laser and LED sources, respectively. The scaling can be thought of as the integral of the normalized PpIX spectrum in this spectral range. The PpIX-weighted equivalents of the dose distributions were calculated using (4), where ΔD was first converted to standard deviation ($\sigma_D$). Then the effective pooled standard deviation ($\sigma_{D,eff,pooled}$, 0.21 $J_{eff}/cm^2$) was determined using (5). The mean effective threshold fluence (0.06 $J_{eff}/cm^2$) was summed with 3× the effective pooled standard deviation to give the effective fluence threshold (0.70 $J_{eff}/cm^2$) used as shown in FIG. 7.

However, the effective fluence threshold only accounts for the availability of light to activate a sufficient amount of PpIX. Since the photodynamic dose is the product of the light fluence and photo-sensitizer availability, the PpIX concentration is needed to calculate the threshold photodynamic dose.

Figure 8A:
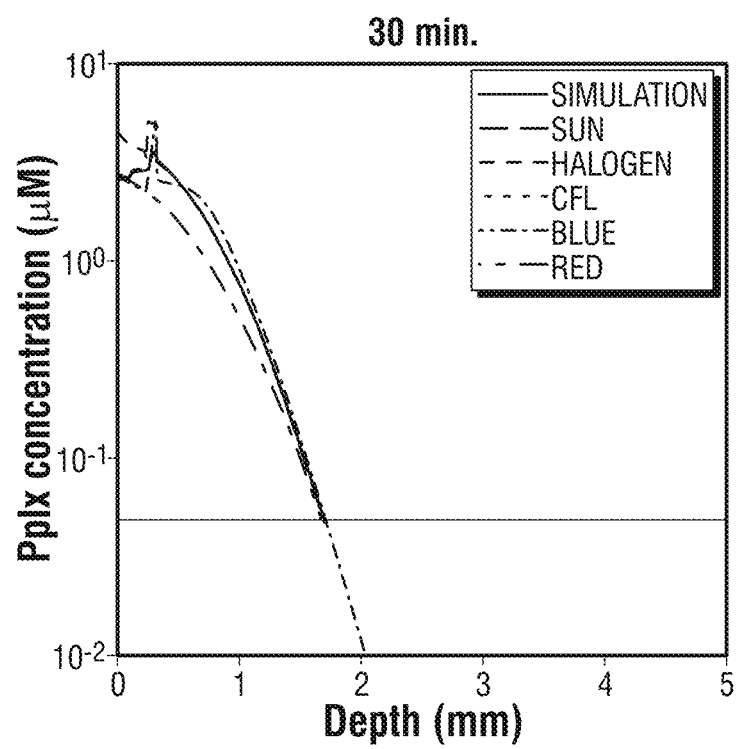
FIGS. 8A and 8B illustrate a model of PpIX concentrations at treatment times of 30 min (FIG. 8A) and 2 h (FIG. 8B) for light treatments with a fluence rate of 35 $mW/cm^2$ for broadband sources, and 100 $mW/cm^2$ for the red and blue sources, where both were incubated for 30 min. The black line represents the threshold PpIX concentration (50 nM).
Figure 8B:
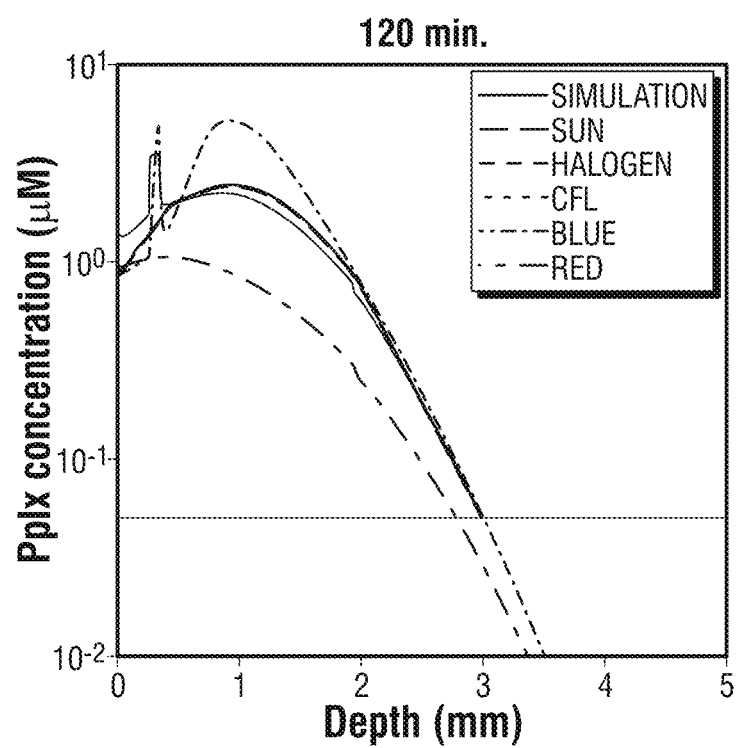
Figure 9A:
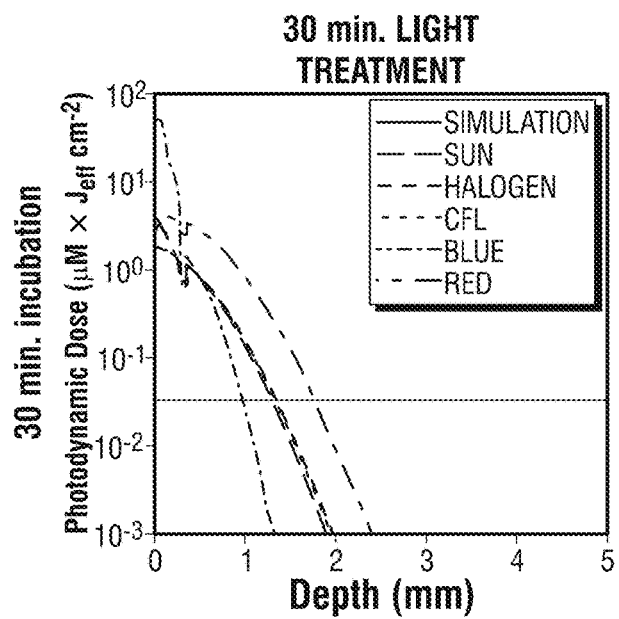
FIGS. 9A, 9B, 9C, and 9D illustrate the photodynamic dose will differ between 30 min (FIGS. 9A and 9C) and 2 h (FIGS. 9B and 9D) treatments, for incubation times of 30 min (FIGS. 9A and 9B) and 2 h (FIGS. 9C and 9D).
Figure 9B:
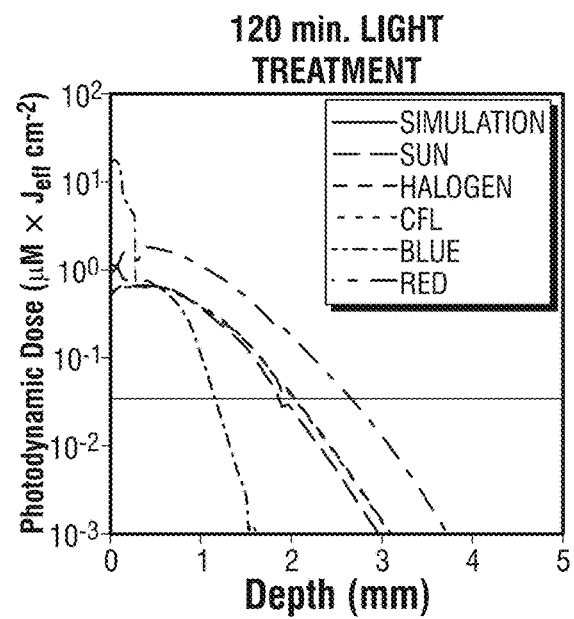
Figure 9C:
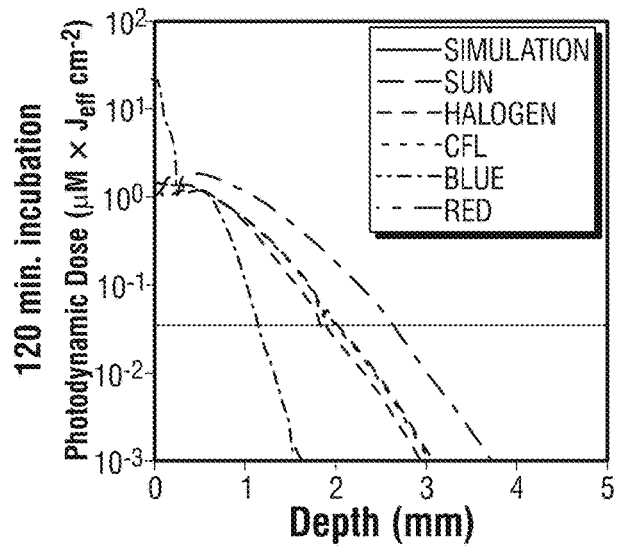
Figure 9D:
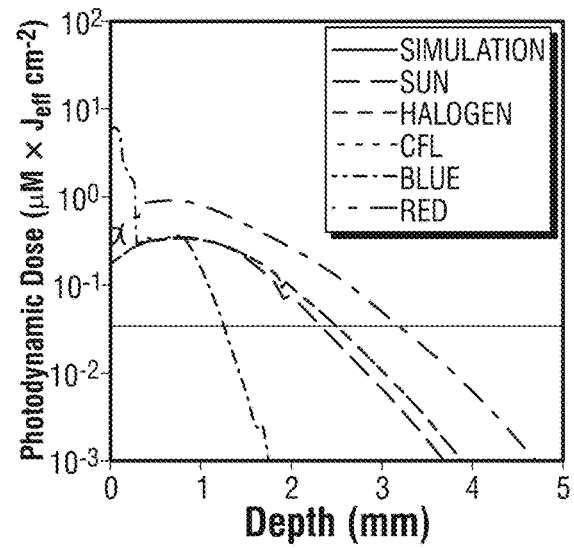

The PpIX concentration at depth in the tissue model was found using equations (6)-(8). The incubation time dictates the initial concentration before photobleaching (8) is considered. Diffusion of the pro-drug during both incubation and treatment allows for deeper PpIX production. Assuming an incubation period of 30 min, which is common in many daylight-PDT protocols, FIG. 8 shows how the PpIX distribution changes over the treatment period, from 30 min to 2 h. The concentration spikes shown in this figure, which are mainly observed in the blue light source, are due to the low-fluence in this tissue layer due to the higher concentration of blood. Using blue-light treatment, with PpIX concentration is higher around 1 mm because of the minimal light penetration, whereas the red-light treatment has lower PpIX concentrations at depth because the red light is able to propagate further into the tissue and cause additional photobleaching.

A threshold PpIX concentration was considered based on literature reports of in vitro and ex vivo studies, which indicate effective cell killing can occur when nano-molar concentrations of PpIX are present. As a conservative measure, a threshold concentration of 50 nM PpIX was chosen for this Example and is shown as the black line in FIG. 8.

The product of effective fluence threshold (0.70 $J_{eff}/cm^2$) shown in FIG. 7 and the threshold PpIX concentration (50 nM) was then calculated. The resulting photodynamic dose of 0.035 u M $J_{eff}/cm^2$ is used as the threshold of cytotoxicity for this Example.

Using the effective fluence estimates, PpIX depth distribution and threshold photodynamic dose, the maximal depth of effective PpIX-activated cell death can be tabulated for each source and at various treatment times (Table 3). Even though the light sources investigated have very different effective surface irradiances, over a 20-min treatment window all light sources are able to activate PpIX at a depth of approximately 1 mm, while the blue LED is just shallow of this and the red LED has a much deeper effect. If only the light fluence is considered for all light sources except the red LED, the depth to reach the fluence threshold within 30 min of treatment is approximately 50-60% less than if the photodynamic dose is considered, whereas for the red LED, the opposite is true and the light fluence over-reports the depth of activation by a similar amount The duration of the incubation time will impact the initial depth distribution of PpIX. Depending on the spectrum and fluence rate of the treatment light, as well as the duration of light treatment, the PpIX distribution will dynamically change during treatment. FIG. 9 shows a representation of how incubation time and treatment time can impact the depth of activation. Longer incubation and treatment times allow for more PpIX diffusion and result in deeper photodynamic effect. The depth of the threshold photodynamic dose is similar for the 30 min incubation with 2 h treatment, compared to the 2 h incubation with 30 min treatment, however the surface photodynamic dose is slightly higher with the longer incubation.

If the desired depth of activation can be estimated, lookup tables for treatment time needed for cytotoxic effect at various depths can also be tabulated (summarized in Table 4). The inputs required to generate this table are the light spectrum, fluence rate, incubation time and desired depth of activation. Table 4 shows a representative example of such a lookup table for the Sun spectrum irradiance values typically seen in different seasons, and for incubation times of 5 or 30 min.

Example 1.6. Discussion

As daylight PDT continues to gain clinical adoption, it will be increasingly important to develop a standard for reporting the administered light dose, especially in the settings where the solar spectrum is known to vary. While the actual absorption spectrum used is not yet fully agreed on, resulting in slight variations in effective irradiance estimates reported by different groups, the method of using the normalized PpIX-weighting factor is the first step to improve repeatability, both clinically as well as between studies.

With narrowband excitation performed during conventional PDT, a simple photodiode-based power meter (Thorlabs PM100D) can be used to measure surface irradiance which should remain relatively constant in the clinical setting. However, the increased variability of broad-spectrum irradiance combined with outdoor treatments have led to the introduction of numerous methods to estimate the spectral irradiance. These data collection techniques have utilized wearable photodiodes, regional weather patterns, lux meters, and spectroradiometers, or simply set a treatment time irrespective of the irradiance.

TABLE 3

Depth (μm) of threshold photodynamic dose for different treatment times after 30 min incubation.

| Light Source | Surface Irradiance (mW/cm²) | Effective Surface Irradiance (mW$_{eff}$/cm²) | 10 min | 20 min | 30 min | 60 Min | 90 min | 120 min |
|---|---|---|---|---|---|---|---|---|
| Uniform | 35.0 | 5.0 | 930 | 1170 | 1270 | 1530 | 1720 | 1830 |
| Sun | 35.0 | 4.0 | 920 | 1160 | 1270 | 1530 | 1720 | 1830 |
| CFL | 35.0 | 1.6 | 940 | 1190 | 1290 | 1560 | 1760 | 1900 |
| Halogen | 35.0 | 0.9 | 940 | 1190 | 1310 | 1590 | 1790 | 2000 |
| Blue | 100 | 73.4 | 760 | 880 | 930 | 1030 | 1090 | 1150 |
| Red | 100 | 1.7 | 1260 | 1600 | 1730 | 2100 | 2400 | 2650 |

TABLE 4

Minimum treatment times needed for PpIX-induce cytotoxicity for various Sun irradiance (350 nm-800 nm) values based on uniformly scaled irradiance measurements taken with Apogee SS-110 and previously reported. Underlined values indicate treatment times between 2-2.5 h, whereas italicized values are treatments over 2.5 h.

| Source | Irradiance (mW/Cm²) | Latitude 45°-60° Daily Avg. | Effective Irradiance (mW$_{eff}$/cm²) | Incubation time (min.) | Treatment time (minutes) needed for PDD threshold | | | | | | |
|---|---|---|---|---|---|---|---|---|---|---|---|
| | | | | | 100 μm | 250 μm | 500 μm | 750 μm | 1000 μm | 1500 μm | 2000 μm |
| Sun | 10 | Winter | 1.1 | 5 | 1 | 4 | 13 | 26 | 50 | <u>126</u> | *>210* |
| Sun | 10 | | 1.1 | 30 | <1 | 1 | 2 | 11 | 25 | 101 | *>210* |
| Sun | 30 | Spring, | 3.4 | 5 | <1 | 2 | 9 | 17 | 33 | 84 | *172* |
| Sun | 30 | Autumn | 3.4 | 30 | <1 | <1 | 1 | 4 | 13 | 59 | <u>147</u> |
| Sun | 50 | Summer | 5.7 | 5 | <1 | 1 | 7 | 14 | 27 | 72 | <u>145</u> |
| Sun | 50 | | 5.7 | 30 | <1 | <1 | 1 | 2 | 11 | 47 | 120 |

While a wearable photodiode seems like an ideal solution for the accurate measure of continuous irradiance, placement of the device proximal to the treatment field can be difficult, and wrist-based systems can introduce additional error. Additionally, the ability to acquire a commercially available device suitable for the clinic is currently limited. Many groups have turned to weather reports and almanac data to provide a generalized estimate of sunlight available at a given location throughout the year, however transient localized weather confounds the ability to predict treatment times. Illuminance measurements with a lux meter have been used by many groups, but illuminance is a measure of light intensity perceived by the human eye, with a peak sensitivity at 555 nm and a weighting of nearly 0 in the UV/blue region. While there has been work to relate solar irradiance with illuminance measurements, the current complexity is prohibitive for most clinical uses. Additionally, illuminance measurements are not ideal for comparing different broadband sources, especially those with a significant UV/blue contribution. Applicants have previously reported collecting continuous measurements using a field-portable spectroradiometer (Apogee SS-110) commonly used in agricultural studies. Measurements of spectrally-resolved irradiance provide the ability to perform PpIX weighting without the introduction of an additional arbitrary weighting inherent in illuminance measurements, however patient positioning relative to the light can still confound results. A previous study showed spectroradiometer measurements introduce the least error (13%) when calculating the effective light dose, whereas other methods can introduce 22-83% error.

Moving further, the tissue optical properties should be considered in addition to PpIX-weighting when estimating the effective light fluence. Even though the PpIX absorption has already been considered at the surface, other tissue chromophores will absorb and scatter light. This fact is further complicated by broad-spectrum light sources.

In this Example, while equivalent surface irradiance was considered for each broadband light source, the resulting effective irradiance showed up to a 5× difference as shown in FIG. 3. Even so, with these substantial differences in effective irradiance at the surface, below the more superficial skin layers (250 μm), the effective fluence of these lights are similar. PpIX absorption is not explicitly addressed in the Monte Carlo simulations because of its negligible effect, so instead a normalized PpIX weighting factor is applied. While inter-patient and infra-patient PpIX production can vary greatly, PpIX production was considered based on previous studies. The effective fluence rate within the tissue model can then be used to estimate the photobleaching effect that occurs during treatment. This was combined with the fluence data generated by Monte Carlo simulations to estimate the photodynamic dose.

The multi-layer tissue model provides the ability to define different optical properties due to the stratified anatomy observed in the skin as shown in FIG. 4 and FIG. 5. One result of this stratified model is observed in FIG. 6 and FIG. 7, where there are two sharp drops in the fluence rate at depths of 250 μm and 1.83 mm. This is due to the higher concentration of blood assumed in these layers. While modeling the blood content as a thin sheet is an oversimplification of the actual anatomy, it shows how various chromophores concentrations can impact the tissue fluence rates. Additionally, the build-up region after each of these regions can be attributed to the increase in refractive index, as observed between the air and skin surface.

It is worth noting the model for the red LED excitation has a more pronounced buildup region in the most superficial layers of skin than the other light sources, which is expected and was summarized in detail in previous studies. Due to the dose buildup observed with longer wavelengths, fluence rates at a depth of 150-500 µm are 57% higher than within the first 10 µm. While this higher fluence rate may be able to activate more PpIX, it also results in increased photobleaching, so for long treatments the total photodynamic dose in this range is not greatly increased.

The incident beam size will also impact the tissue fluence rate. This effect is depth-dependent and more pronounced with longer wavelengths, where Applicants' model indicates a 21 cm beam at the surface, corresponding to 25 mm radius source, will have 1.1-1.7× greater fluence within the same voxel space than a beam with surface area of 1 cm. This Example used the larger spot size (25 mm radius source) to better simulate field illumination as used in daylight-PDT protocols. While clinically, actual field illumination area may be larger, for this simulation the 21 cm illumination area is sufficiently larger than the 1 cm voxel area used to track photon interactions.

Considering both the available light and the dynamically changing PpIX concentration at depth in tissue, is a complex procedure in clinical practice. The complexity of considering these factors needs to be reduced to a clinically digestible format. To that end, Applicants propose the use of a lookup table that can be used in the clinic to modify light treatments. While Table 3 provides an estimate of the depth of potential PpIX activation as a function of treatment time for each light source considered in the current Example, the Example in Table 4 is likely more clinically applicable.

Since it is likely the light irradiance will fluctuate, Table 4 provides clinically-relevant dose planning information to define treatment times required to achieve activation at specific depths for each of the light sources over a range of irradiance values and PpIX incubation times. Table 4 also has a column to indicate the seasons most commonly associated with the given irradiance for latitudes between 45 and 60° based on measurements previously reported where lower latitudes would have a higher average irradiance. These seasonal variations are based on historical data for specific locations, so daily weather patterns should still be considered when planning daylight-PDT treatments.

The proposed clinical workflow involves the clinician determining the type of skin lesions that needs treatment and using their judgment to estimate the depth. Using the depth estimate, a specific light source, and a simple measurement of the total irradiance, the information can be used to estimate a desired incubation and minimum treatment time. If conventional-PDT is desired, longer incubation times with narrowband light sources may be considered, whereas for daylight-PDT shorter incubation times would be used. From these lookup tables it can be observed that blue light is unable to have a photodynamic effect much beyond 1 mm, irrespective of incubation time. However, for deeper lesions (>1 mm) longer incubation may be required to allow activation within a 2 h window. Ultimately, it is up to the clinician to understand the clinical presentation and determine which light or light combination would be appropriate for treatment For example, a more superficial AK may benefit from light with additional light dose deposited superficially, whereas a nodular BCC could benefit from a boost of red light to activate PpIX at deeper layers.

While pathology examples presented in FIG. 8 and Table 1 show AK and BCC with depths of less than 500 µm, which according to the lookup table, would take minimal time to treat, it is important to remember the times reported are to reach the minimum threshold photodynamic dose. So longer treatment times would still be appropriate. While not all the lesions shown in FIG. 2 are commonly treated with PDT, it provides evidence that the effective photodynamic range in tissue could be sufficient to cause some cell death. So further investigations may be appropriate.

Further dermopathologic characterization of AKs and BCCs could help improve the Monte Carlo geometry used in this Example. Chromophore concentrations observed in neoplastic tissues, along with more refined stratification of layers, may prove useful in improving fluence estimates. Additionally, detailed investigation of pro-drug diffusion rates and PpIX production rates in these tissue samples could help better estimate the photodynamic dose.

The lookup tables presented in this Example could be further modified to include factors such as lesion type, estimated depth, melanin content and PpIX production rate. The choice would then be to measure the surface irradiance of a light source with known spectrum and estimate the desired depth of activation. Using these two values the treatment time of a single light source or light combination could then be prescribed. This type of lookup table is something that could easily be included in a web or phone-based application or further automated in a tool used to measure spectral irradiance.

Example 1.7. Conclusions

This Example presented the application of a 7-layer Mote Carlo model to estimate the light fluence in tissue for multiple light sources that have been previously reported for use in PpIX-PDT. The commonly used weighting factor based on the PpIX absorption spectrum was used to find both the effective irradiance at the skin surface as well as the effective fluence rate in tissue. The effective fluence rate was then used to find the total effective fluence for various treatment times. An effective fluence threshold (0.70 $J_{eff}/cm^2$) was introduced based on a meta-analysis of previously published ALA-PpIX induced cell death. The PpIX concentration was estimated for various incubation and treatment durations for a range of fluence rates. Using the product of this fluence threshold and an estimate for the threshold concentration of PpIX (50 nM), a photodynamic dose of 0.035 u M $J_{eff}/cm^2$ is used as the threshold of cytotoxicity. The depth of PpIX-induced cytotoxicity was estimated for various treatment times for each light source at the investigated irradiance values. Even though there was up to a 5× reduction between the effective surface irradiance of the broadband light sources, the effective fluence below 250 µm was relatively equivalent. Clinically-relevant lookup tables were introduced to provide a simplified method to estimate treatment times for various light sources over a range of irradiances. From these lookup tables it can be observed that blue light is unable to have a photodynamic effect much beyond 1 mm, irrespective of incubation time. However, for deeper lesions (>1 mm) longer incubation may be required to allow activation within a 2 h window. The data provided in the lookup tables is compared to clinically relevant histopathology samples to provide context on clinical applications. It is readily envisioned that this model could be extended to include common disease morphologies, melanin contents and PpIX production rates.

Example 2. Weather-Informed Light-Tissue Model-Based Dose Planning for Indoor Daylight Photodynamic Therapy This Example describes the use of a weather-informed light-tissue model-based dose planning for indoor daylight photodynamic therapy.

Daylight activation for photodynamic therapy (PDT) of skin lesions is now widely adopted in many countries as a less painful and equally effective treatment mechanism, as compared to red or blue light activation. However, seasonal daylight availability and transient weather conditions complicate light dose estimations. A method is presented in this Example for dose planning without placing a large burden on clinical staff, by limiting spectral measurements to a one-time site assessment, and then using automatically acquired weather reports to track transient conditions. The site assessment tools are used to identify appropriate treatment locations for the annual and daily variations in sunlight exposure for clinical center planning. The spectral information collected from the site assessment can then be integrated with real-time daily electronic weather data. It was shown that a directly measured light exposure has strong correlation ($R^2$: 0.87) with both satellite cloud coverage data and UV index, suggesting that the automated weather indexes can be surrogates for daylight PDT optical dose. These updated inputs can be used in a dose-planning treatment model to estimate photodynamic dose at depth in tissue. A simple standardized method for estimating light dose during daylight-PDT could help improve intersite reproducibility while minimizing treatment times.

Example 2.1. Introduction

Using daylight as an activation mechanism for photodynamic therapy (PDT) of skin has been investigated over the past decade, and is now widely accepted in several countries, as a less painful and equally effective treatment mechanism when compared to conventional red or blue light activation. However, seasonal daylight availability and transient weather conditions complicate light dose estimations, especially in northern latitudes. Clinically, appropriate treatment months are identified based on latitude and season, and patients are treated for approximately 2 h where appropriate sunlight is expected. Yet, the changes in solar irradiance due to the time of day and transient weather conditions confound reproducibility. In this Example. Applicants supply a method involving a one-time site assessment is proposed combined with programmatically acquired weather data to provide real-time estimates of light fluence rates and photodynamic dose at depth in tissue.

Daylight PDT and similar low-fluence rate activation methods have been reported to be less painful than conventional PDT. Additionally, the ability to treat multiple patients simultaneously has economic benefits in certain healthcare systems. While lights used in conventional treatments are regulated medical devices that have well-characterized narrowband spectra and fluence rates, daylight is broad spectrum and the fluence rate changes on a continuous basis. Despite these well-known fluctuations, daylight PDT is an approved treatment in many countries without explicit guidance on dealing with daily weather prediction. While reasonable approaches to delivering daylight PDT are always implemented, a more formalized approach to estimating light potential seems warranted.

With the variable nature of sunlight versus cloud, it is natural to question how much light is required to deliver an appropriate photodynamic dose. An international consensus has been provided to supply guidance on the minimum effective fluence needed to activate PpIX and provides a table of appropriate treatment months based on latitude. A previous model developed provides a method for estimating the PpIX-weighted light fluence based on a simple low-cost lux meter measurement. While weather conditions have been reported in past studies, the recorded parameters are not standardized. Many clinical teams have patients sit outside for a fixed 2-2.5 h period, but it is still unclear whether clearance could be achieved with less time, or conversely whether more time would be beneficial. Additionally, intersite comparisons and reproducibility become an issue when the continuous irradiance rate is not considered. The following sections in this Example describe methods to improve dose planning without placing a large burden on clinical staff, by limiting spectral measurements to a one-time site assessment, and then using automatically acquired weather reports to track transient conditions during daylight treatments. These methods can be applied to both indoor and outdoor daylight treatments, where indoor treatments provide the added benefit of reliable climate control and reduce the need to apply sunscreen due to the UV-blocking nature of many windows; however, the spectral changes introduced by this barrier need to be characterized for proper light dose estimation.

Example 2.2. Materials and Methods

Figure 10A:
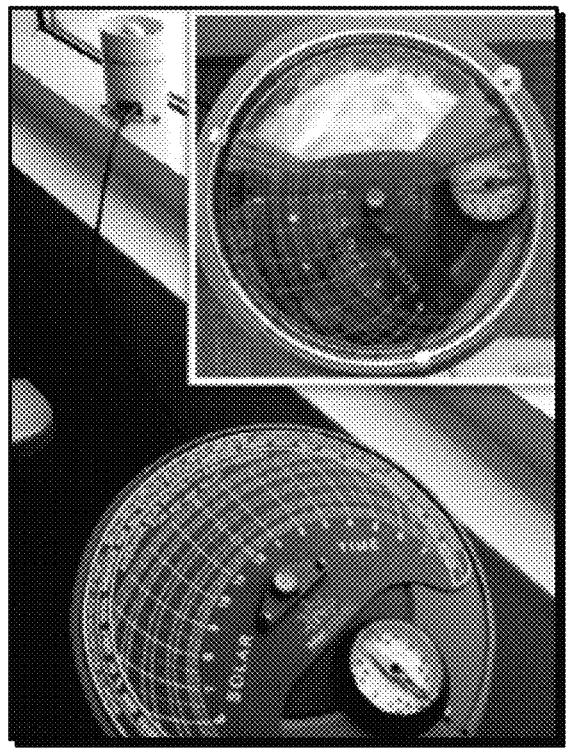
FIGS. 10A, 10B, and 10C illustrate a Solar Pathfinder device showing compass alignment and nearby spectroradiometer (FIG. 10A), where the clear plastic dome (inset) reflects the sky. The outline of obstructions is traced (light green-shaded region, FIG. 10B) and recorded indoors in a south-west facing window, which can then be converted to a binary grid of sunny and shaded regions (FIG. 10C). As a comparison, the same procedure was conducted in an area outside of the building (FIG. 10C, inset) where morning sunlight was available, but tall trees to the west blocked the afternoon sun.
Figure 10B:
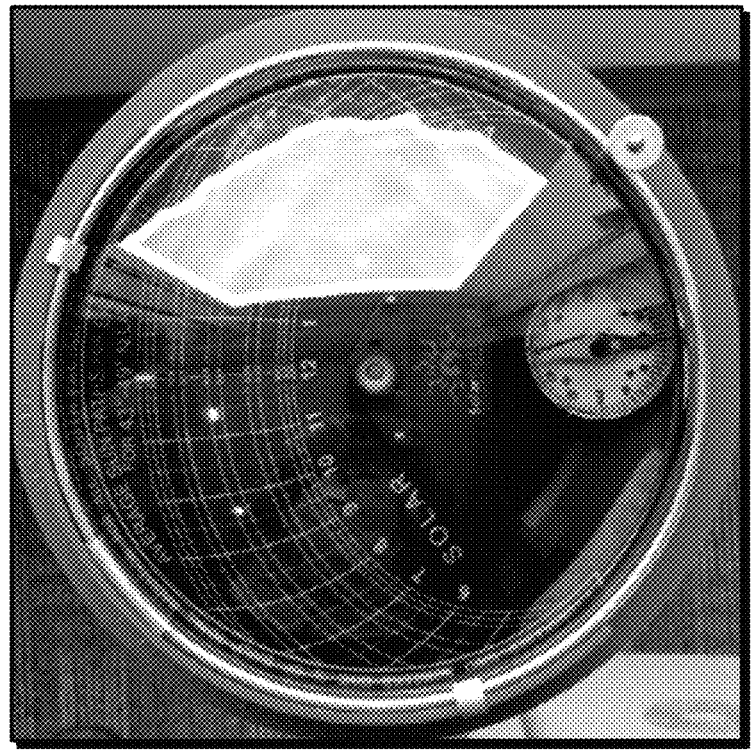

A solar site analysis was performed using a Solar Pathfinder (The Solar Pathfinder Company, Linden, Tenn.), which is a basic tool commonly used in the photovoltaic industry to site solar panels for maximal annual exposure. The tool is composed of a grid showing solar time (vertical lines) which are intersected by months (horizontal lines) as shown in FIG. 10A. The grid is specific to a range of latitudes and printed as white lines on black paper. The base is oriented such that the paper grid fits in the plastic base at a specific orientation, and the whole system is aligned using a built-in compass. A clear plastic dome with open sides is placed on top of the base (FIG. 10A inset, B). A white wax pencil is used to mark the paper grid to denote the boundaries of objects blocking the reflected sky (FIG. 10B, green outline). The grid is then removed from the base, and the times and months indicated by markings are entered into a spreadsheet, which is visualized in FIG. 10C.

A field spectroradiometer (SS-110; Apogee Instruments. Logan, Utah) was used to collect spectral data at 5 min time intervals over the course of multiple weeks. Calibration of the device was performed by the manufacturer using National Institute of Standards and Technology (NIST) traceable light sources. The device was leveled and placed on a window sill in close proximity to where the site assessment was performed and where patients are to be treated (FIG. 10A, upper left). The total irradiance was calculated by integrating spectral measurements between 350 and 800 nm.

A weighting based on the absorption spectrum of PpIX was used to find the effective irradiance. The PpIX absorption spectra were first normalized and then multiplied by the spectroradiometer measurements. This provides a metric of the PpIX-weighted effective irradiance, which, when combined with treatment time, provides the effective light dose.

Using a Python script to interface with an application programing interface (API), hourly weather data were programmatically accessed from weatherbit.io for an airport approximately 5 km from the treatment site. These data provide formatted key-value pairs of various weather parameters. The main values considered are a model-based solar irradiance estimate assuming clear skies, percentage of cloud coverage based on satellite imagery, and UV index.

Temperature and humidity values are also provided; however, they only need to be considered for outdoor treatments.

Example 2.3. Results

Figure 10C:
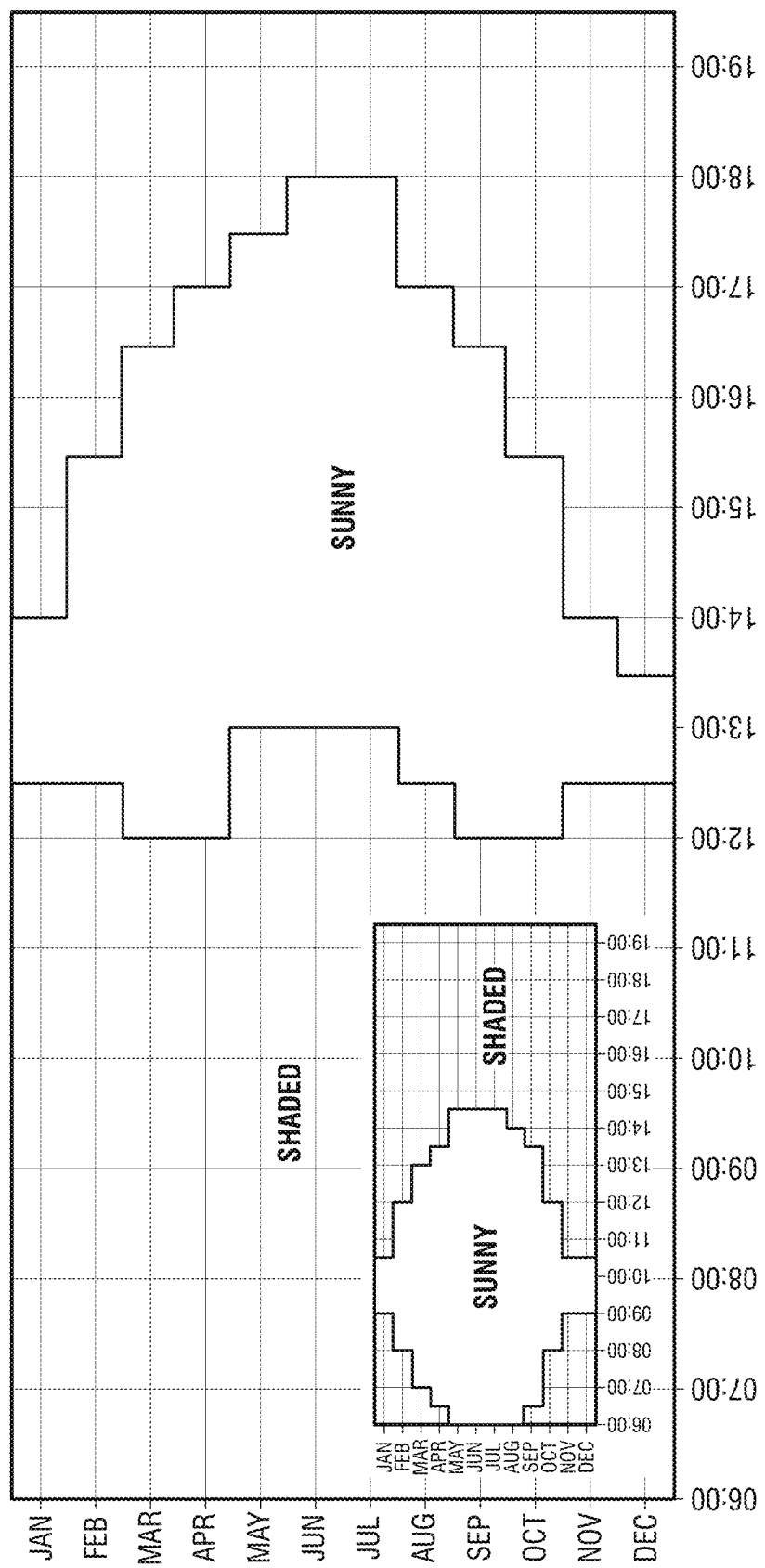

The solar site analysis was performed in the waiting area of the Dermatology Clinic at Dartmouth Hitchcock Medical Center in Lebanon, N.H. (latitude 43.6° N). This area is on the 2nd floor and has large southwest-facing windows. The analysis shows there are between 1 and 5 h of direct sunlight each afternoon for this location (FIG. 10C). During the months of mid-April through mid-August, there is a decrease in noontime sunlight due to the building awning. Mid-October through mid-January have less than 2 h of direct sunlight due to the building orientation. A site assessment was also conducted in a nearby picnic area where the sky was unobstructed in the morning, but tall trees just to the west blocked afternoon sunlight (FIG. 10C inset).

Figure 11:
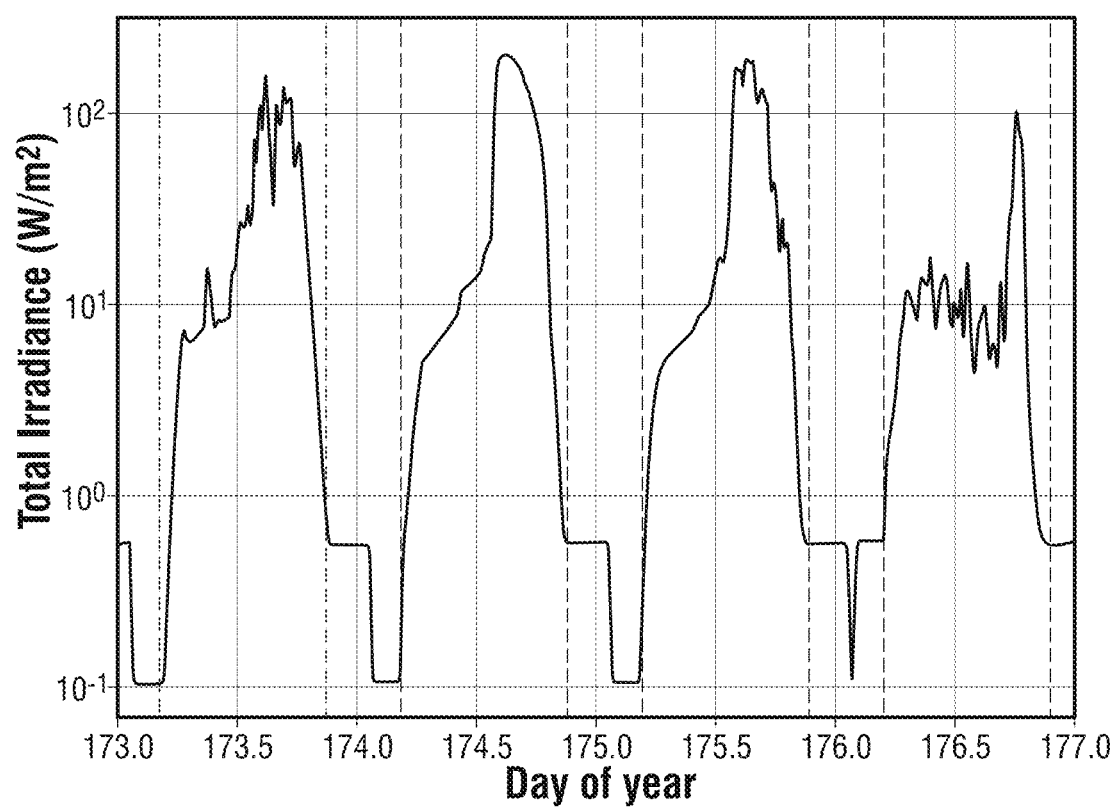
FIG. 11 illustrates solar variation from total irradiance measurements taken at 5 minute intervals over approximately 5 days, showing high irradiances only in the afternoon hours (pink-shaded area) and at least an order of magnitude less in the mornings (blue-shaded areas).
Figure 12B:
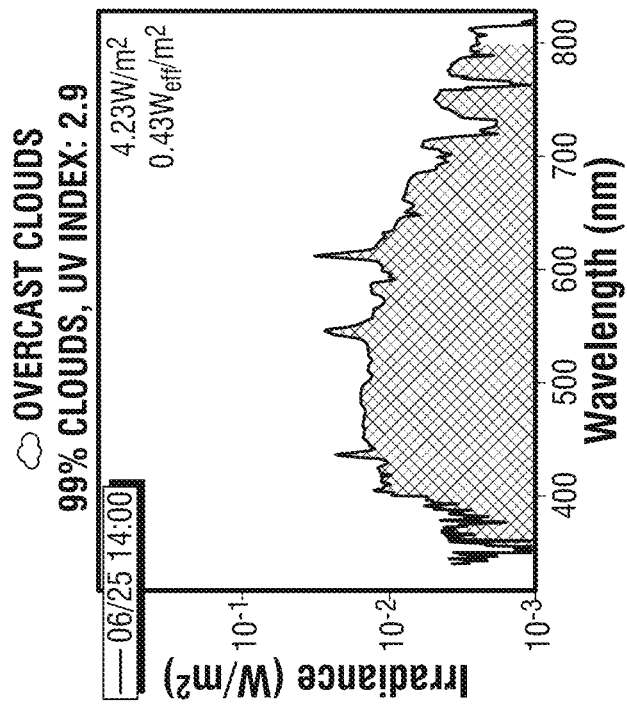
FIGS. 12A, 12B, 12C, and 12D illustrate spectroradiometer measurements taken at 14:00 on a clear day in June (FIG. 12A), a cloudy day the same week (FIG. 12B), a clear day in October (FIG. 12C), and a partly cloudy day in October (FIG. 12D). The weather report is shown in the upper left of each graph, and the total irradiance and PpIX-weighted irradiance are given in the upper right.
Figure 12A:
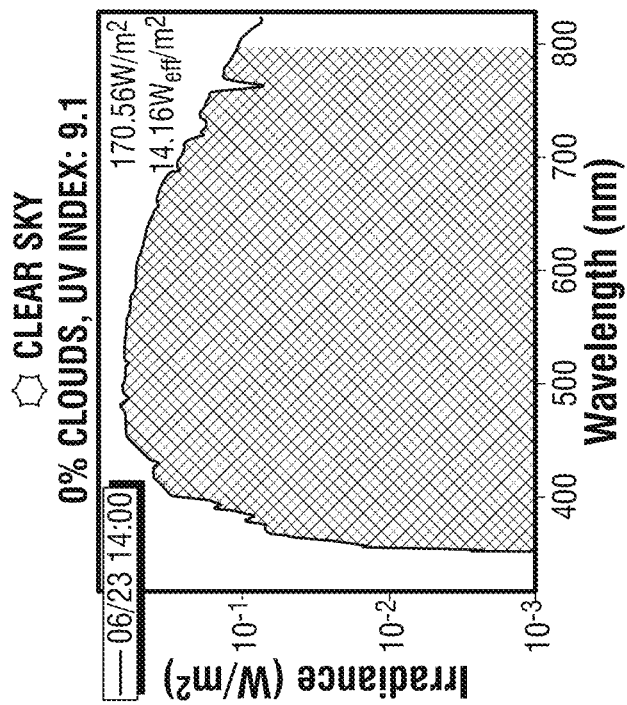
Figure 12D:
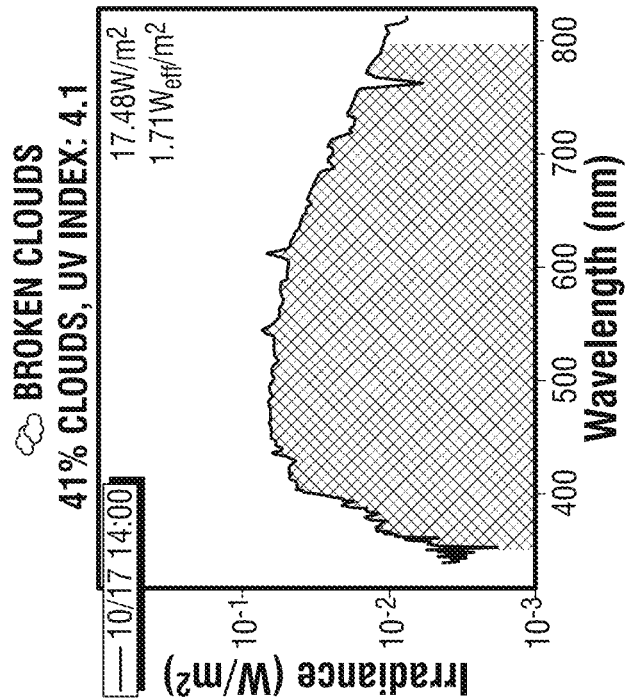
Figure 12C:
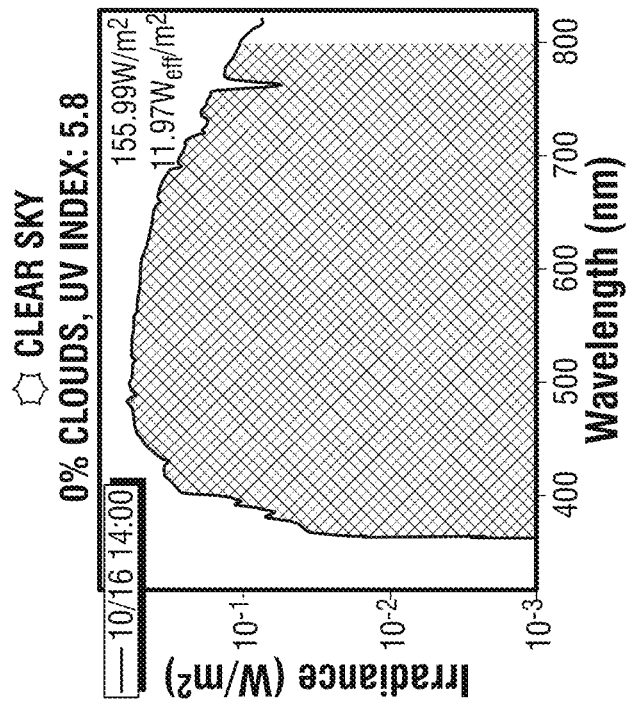

As an example of the variability observed in the total irradiance, measurements collected over a 5 day period are provided in FIG. 11, where the blue-shaded regions are in the morning when the building blocks direct sunlight, and the red-shaded regions are the direct afternoon sunlight. The first day shows how cloudy conditions can impact the irradiance. A clear day and mostly clear day are shown on the 174th and 175th days of the year, respectively, while day 176 is mostly overcast. Even on the clear day, the total irradiance can fluctuate over a 2 h window and the peak irradiance is only observed over a short period of time. The horizontal lines during the night represent the base-line indoor lighting, which is turned off just after midnight most nights.

While FIG. 11 shows the total irradiance at 5 min time resolution, FIG. 12 provides representative examples of the spectral distribution at 14:00 on days in different seasons and with different weather conditions. FIG. 12A provides the spectral characteristics measured indoors on a clear day in mid-June, whereas FIG. 12B is on an overcast day the same week. The overcast day reports just 2% of the total irradiance for the same time two days before. To compare seasons, FIG. 12C provides spectral measurements for a clear day in mid-October, where the overall total irradiance is slightly less than June, but still sufficient for treatment. However, a partly cloudy day in October has approximately 10% as much light. The indoor CFL lights can be observed in FIG. 12B (spectral peaks at approximately 440, 560, and 610 nm) and provide a significant portion of the irradiance due to the overcast conditions at that time.

Figure 13A:
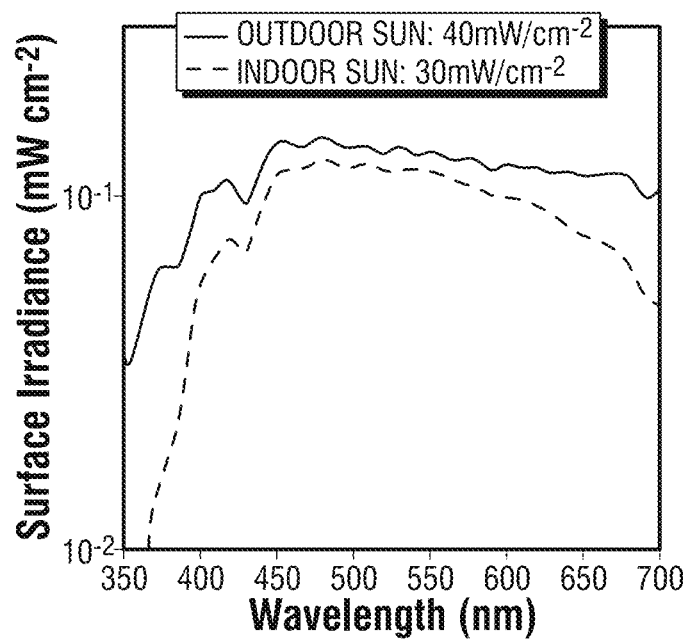
FIG. 13 illustrates scaled daylight spectra measurements of outdoor and indoor daylight (FIG. 13A) and their PpIX-weighted counterparts (FIG. 13B). Snapshots of photodynamic dose after 30 minute incubation for various treatment times (outdoor: solid; indoor: dotted) (FIG. 13C) and their corresponding maximal depth of effective photodynamic-dose (PDD) (FIG. 13D) is also shown.

Using the spectroradiometer measurements with Applicants' light-tissue model, an estimate of the photodynamic dose at depths can be determined. This was performed for daylight spectra collected both outdoors and indoors. The spectral measurements are shown in FIG. 13A, where for comparison purposes the intensities were uniformly scaled such that the indoor irradiance is 75% of the corresponding total outdoor irradiance, which is similar to reports by others. The actual reduction is dependent on the transmission of the glass or acrylic barrier, which is concisely summarized for many common materials.

Figure 13B:
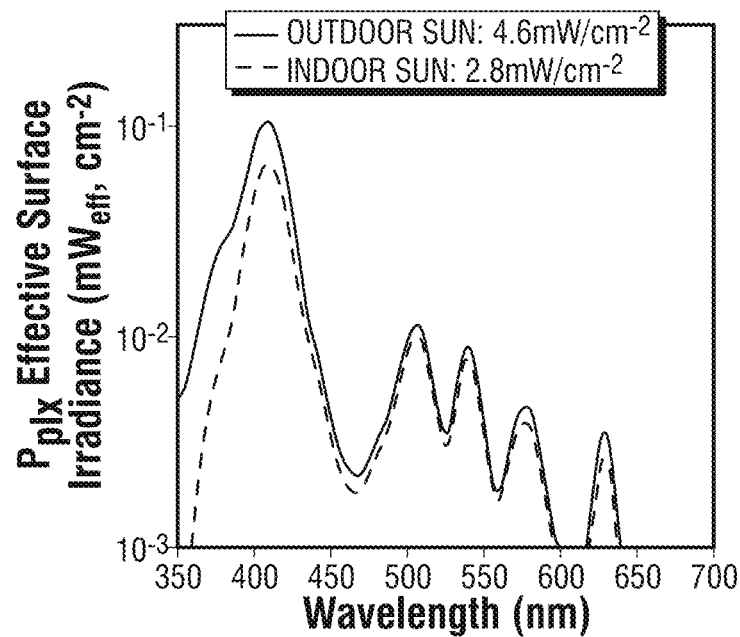
Figures 13C, 13D:
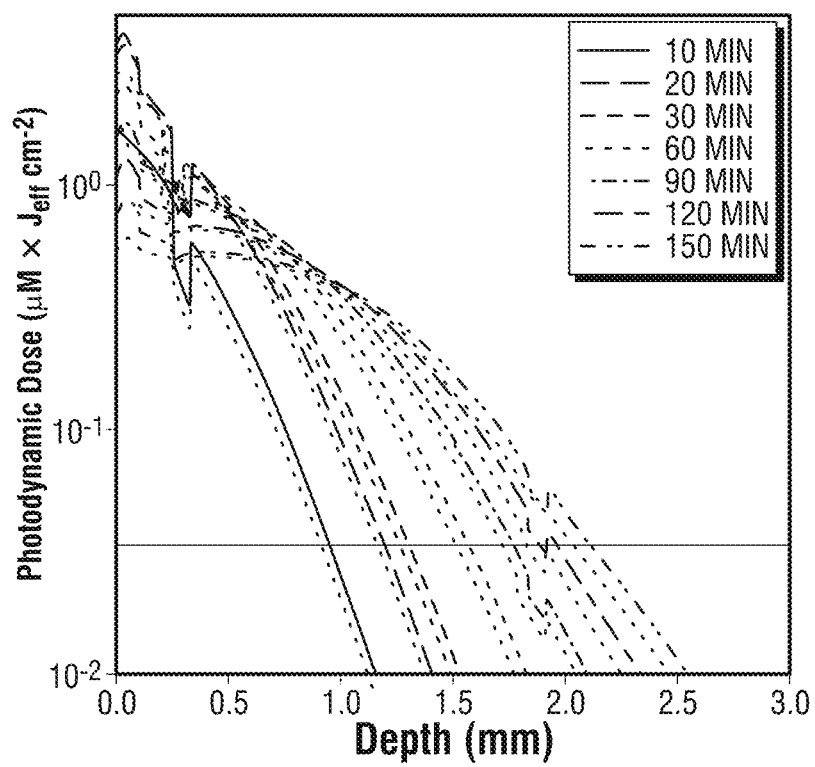

Most investigations of daylight PDT report light dose as the effective fluence, which is the fluence weighted by the PpIX absorption spectrum. So, even though the total irradiance of indoor daylight is 75% of its outdoor counterpart, the PpIX-weighted effective irradiance indoors is 60% of the outdoor complement because more UV light is blocked by the window (FIG. 13B). While the PpIX effective irradiance aims to account for the spectral characteristics of broad-spectrum activation, when these irradiance values are used to estimate photodynamic dose (PDD) at depth in tissue after a 30 min incubation period, where a combination of fluence rate, PpIX production rates, photobleaching, and time is considered, the overall depth of activation is largely similar (FIG. 13C-FIG. 13D).

Figure 14A:
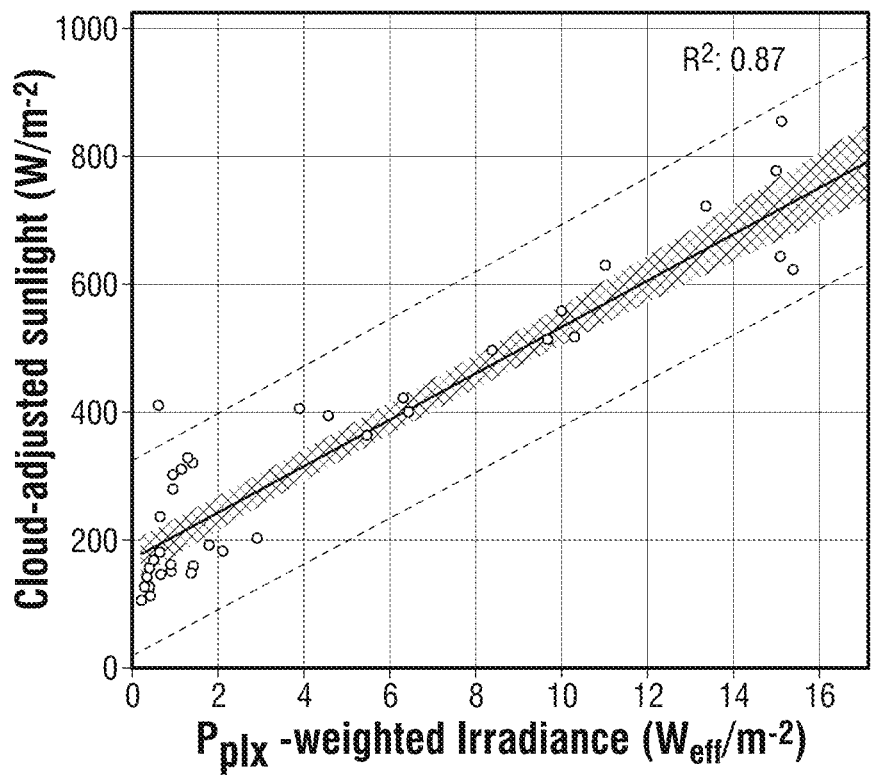
FIGS. 14A and 14B illustrate comparison of indoor PpIX-weighted spectroradiometer measurements (x-axis) and cloud coverage (FIG. 14A) and ultraviolet (UV) index (FIG. 14B), where the blue-shaded region provides a 95% confidence interval and the dashed lines provide the 95% prediction limits.
Figure 14B:
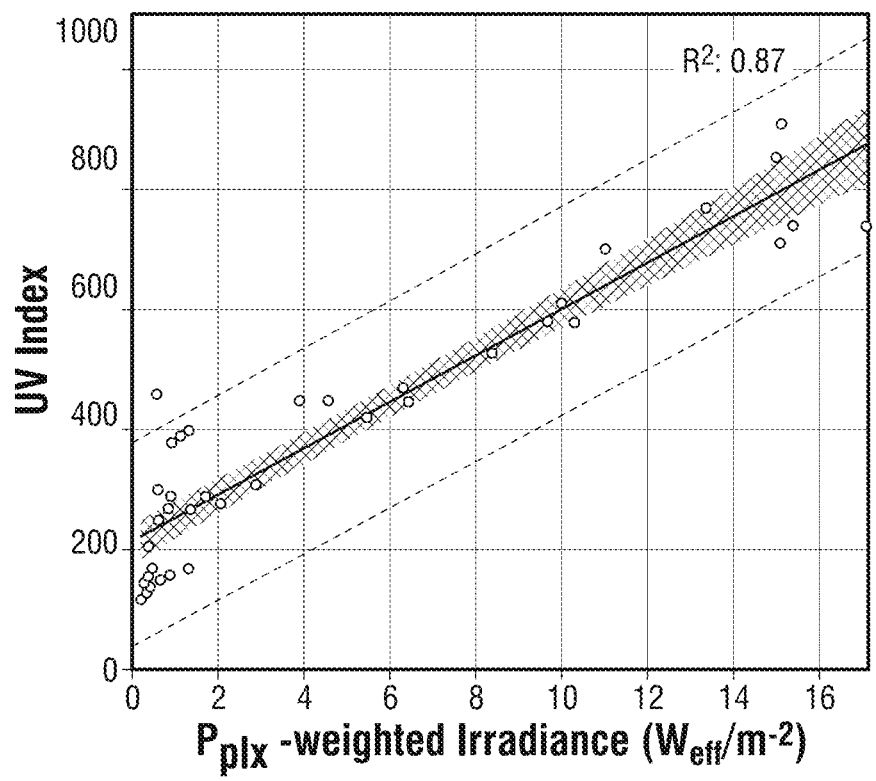

To determine whether specific weather-based metrics could be used as surrogate for spectroradiometer measurements, time-correlated measurements were compared with corresponding weather data. Spectroradiometer measurements were averaged for over a 10 min window around each new hour for times that were previously determined to be in the "Sunny" region of FIG. 10C. These irradiance values were then compared to the product of the cloud percentage and the modeled ideal sunlight (FIG. 14A), or the ultraviolet (UV) index (FIG. 14B), reported by the weather station at the local airport. When only the modeled sunlight is assumed, the correlation is poor ($R^2$: 0.49, not shown), but both the cloud-corrected sunlight and UV index show a strong correlation ($R^2$: 0.87).

Example 2.4. Discussion

While weather data have been incorporated in previous studies of daylight PDT, the reporting mechanism is not standardized. Other have asked patients to record weather conditions based on a 1-5 scale and retrieved maximal UV index during the treatment from an external source. That study further found UV index could not be used as a predictor of daylight PDT light dose. However, these results may be limited by the reporting mechanism, whereas Applicants' more specific time-correlated method indicates a correlation. A recent review found there have been no clinical studies showing an impact of average daylight light dose on daylight-PDT efficacy, once a minimal threshold is met. While Applicants' model indicates there is a link between total light fluence and photodynamic dose, it also indicates treatment could be sufficient in well under 2 h on many sunny days, and even some cloudy days in the summer.

Before implementing a daylight PDT protocol, a site assessment should be performed ideally, to verify potential light exposure. Seasonal variations in the solar path at the treatment location are important to understand and various sites may have better seasonal or daily value. While the current Example proposes an indoor daylight PDT protocol so the building orientation is the driving factor, outdoor treatments could have similar obstructions and can be vetted in the same manner. The seasonal solar availability at specific sites can be used for long-term clinical scheduling. For example, in Applicants' case the sun was generally available only in the afternoon so patients should only be scheduled during this period; however, an outdoor site near the building was identified that provides daylight from the early morning through mid-afternoon. Just as clinical procedures are scheduled in specific rooms, daylight-PDT locations could be scheduled based on solar availability of the site.

While seasonal solar availability is one aspect of a site assessment, another is the spectral characteristics of the location. The spectral characteristics of daylight behind a glass window or outside are different, especially in the UV region. Spectroradiometer measurements taken during a site assessment can be used as an input to Applicants' model-based dose-planning tool. Using this tool with the input spectra, an estimate of photodynamic dose at depth in tissue can be obtained for different incubation and treatment periods.

Since the primary spectral changes introduced by a clear barrier are a reduction in UV-blue light, the PpIX-weighted effective irradiance will be reduced to a greater degree than the total irradiance changes. However, since these spectral changes are UV-weighted, their impact at depth in tissue will be minimal and changes in the photodynamic dose will primarily be localized to the first few hundred microns of tissue. It is also interesting to note that as the treatment time increases, there is more photobleaching at superficial tissue layers, so the overall photodynamic dose at specific treatment times is reduced near the surface. Even though the indoor effective irradiance is reported to be 60% of the outdoor counterpart, the PDT dose at depth remains equivalent beyond the first 200 μm of tissue. Additionally, within the 15 min of treatment after a 30 min incubation, there is sufficient photodynamic dose to depths of approximately 1 mm for the given irradiance; however, to treat the next mm, the treatment time needs to be lengthened by 10×.

While indoor daylight PDT requires less vigilance in applying sunscreen, careful consideration should be taken when choosing a sunscreen for outdoor treatments. The chosen sunscreen should not block wavelengths that are predominantly absorbed by PpIX. If sunscreens are applied, this model would need to be adjusted to account for higher light scattering in the superficial layers of the multilayer skin model. In some cases, a glass gazebo has been used to block UV and reduce the need for applying sunscreen effectively providing indoor daylight. With treatment locations that are identified to have full-day sunlight, the spectral composition of UV light will change throughout the day, which should be considered when performing the one-time site assessment.

The light dose given during daylight PDT is often reported to be 2-2.5 h in a range of weather conditions, seasons, and latitudes. While others have placed a wrist-based dosimeters on patients, the ideal dosimeter would be placed on the treatment site, yet current technology and large treatment fields have made this impractical. It may be feasible to place a spectroradiometer near a patient being treated to provide better estimates of light dose, which can then be correlated with clearance; however, this is still slightly cumbersome and impractical.

As a middle-ground solution for improved dose planning, Applicants propose a one-time site assessment. After this site assessment, weather data can be used as a surrogate for continuous spectroradiometer measurements. While seasonal and in some cases weekly or daily variations have been presented previously by others as a way to determine whether sufficient sunlight is available. Applicants have shown transient weather conditions will impact the light availability (FIG. 11 and FIG. 12). However, by collecting weather data at a higher time resolution that more closely aligns with the treatment period, a more accurate light dose estimate can be obtained. Using either satellite data for cloud coverage or UV index provides a strong correlation with spectroradiometer measurements (FIG. 14). This method can be used for both indoor and outdoor daylight PDT protocols.

Weather data can be acquired programmatically and are generally available from many locations such as airports. This automated process could easily be incorporated into an application on a mobile device, so real-time dose estimates could be obtained with minimal effort. Furthermore, the weather data can be used to estimate the light fluence rate based on the spectral data from the one-time site assessment. This can be used with the lookup tables generated by the dose-planning model, so real-time estimates of photodynamic dose at depth can be monitored. As weather forecasts become more accurate, the same method could transition from dose estimation to a dose-planning mechanism.

Example 2.5. Conclusions

Measuring light dose during daylight PDT is difficult due to a number of masons, including the length of treatment, broad spectral characteristics, seasonal changes, site latitude, and continuously variable weather conditions. It is unrealistic to expect the clinical team to monitor these factors continuously during treatments, and as a result, many treatment periods are set to 2 h. Yet, for the sake of reproducibility, quantifying the light dose is important to better understand the depth of treatment and potential clearance. Applicants propose methods to improve dose planning without placing a large burden on clinical staff, by limiting spectral measurements to a one-time site assessment. Furthermore, automatically acquired weather data can be used to routinely account for transient conditions during daylight treatments. Using these data in a model, a lookup table can be generated to propose minimal treatment times based on the desired depth of treatment. A simple standardized method for estimating light dose during daylight-PDT could help improve intersite reproducibility while minimizing treatment times and optimizing clearance rate.

Example 3. Additional Embodiments

This example describes additional embodiments according to various aspects of the present disclosure.

The prevalence of actinic keratosis (AK) is estimated to be between 11% and 26% in the United States resulting in an annual management burden of approximately $1 billion. In the population between ages 60 and 69 years, those affected by AKs increases to as high as 80%, and while the disease is not life threatening the high prevalence introduces a significant disease burden. If left untreated, AKs risk progressing to invasive squamous cell carcinoma (SCC), which is 1.5-11× more likely in patients with multiple lesions. AKs are most common in sun-exposed areas of skin in older populations, while immunosuppressed patients are 250× more likely to develop AKs. As such, AKs are generally treated as carcinoma in situ with the assumption they will progress into SCC.

TABLE 5

Summary field-directed AK treatments.

| Therapy | Scheme | Benefits | Drawback |
| --- | --- | --- | --- |
| Fluorouracil (5-FU) | 1-2/d for 2-4 weeks | Simple to apply | Pain, pruritus, burning, erythema, erosion, inflammation |
| Diclofenac | 2x/d for 90 days | Few side effects | Long duration |
| Chemical peeling | 1 or more times | Rapid technique | Superinfection, inflammation, abnormal pigmentation, scarring |
| Imiquimod | 1x/d- 3x/week for 2-4 weeks | Higher rate of clinical clearance | Erythema, scabbing, erosion |
| MAL or ALA-PDT | 1 or more times | Good cosmetic results | Pain, erythema, inflammation, hypochromia |

TABLE 5-continued

Summary field-directed AK treatments.

| Therapy | Scheme | Benefits | Drawback |
|---|---|---|---|
| Ingenol mebutate | 1x/d for 2-3 days | Shortest duration | Not modifiable side effects |

Treatment modalities can be categorized as lesion-directed or field-directed, where lesions-directed treatments physically destroy visible lesions using methods such as surgery or cryotherapy, which often result in scarring. However, field carcinogenesis is common in AK progression due to the correlation with chronic ultra-violet (UV)-exposure, resulting in multiple lesions, including early-stage disease which is particularly difficult to visualize. Thus, field-directed therapies are needed to treat large areas, commonly on the face, scalp, neck and extremities, where clinically prescribed methods are summarized in Table 5. The most common field treatments are 5-fluorouracil (5-FU) and aminolevulinic acid (ALA) photodynamic therapy (PDT) (ALA-PDT), where 5-FU requires patients to apply a cream 1-2× per day for up to a month. While conventional PDT reports high pain, daylight PDT reduces this significantly. Additionally, erythema and inflammation are seen for up to 48 hours after PDT treatment, however similar side effects are seen over the longer duration of 5-FU treatments. Ingenol mebutate provides treatment over shorter duration, but the high price and potential for non-modifiable side-effects have reduced clinical adoption.

The topical pharmaceutical used in PDT skin treatment is the pro-drug aminolevulinic acid, which exhibits unbiased diffusion into all skin, but is selectively metabolized by just the neoplastic cells and converted into the photosensitizer protoporphyrin IX (PpIX). During conventional treatment ALA is often left to incubate under occlusion for 1-3 hours. After incubation the PpIX is activated either using a blue light at the peak spectral absorption (410 nm), or by red light at a lesser-absorbing Q-band (630 nm). When activated, PpIX produces locally cytotoxic reactive oxygen species, as well as fluorescence emissions.

Models considering light fluence in tissue can be used to estimate the depth-distribution of photodynamic dose, which is currently difficult to quantify for broad-spectrum activation, such as daylight. The rate of PpIX production is widely variable both spatially and between patients. Fluorescence imaging before and after ALA incubation can provide quantitative measures of available PpIX and is strongly correlated with lesion clearance. While fluorescence imaging has the ability to quantify PpIX production, the clinical translation of this approach has been limited due mainly to device size and cost.

High pain levels (>5, on a scale of 0-10) have been reported with conventional PDT, which are thought to be related to the long incubation times and high fluence rate activations, however much lower levels (<2) have been reported using short incubations and daylight activation. The report of decreased pain and similar efficacy have driven the increased clinical adoption of daylight-PDT in Europe.

Additionally, without the need for expensive clinical light sources, more clinics have been able to adopt this methodology. Without the bottleneck of a single treatment lamp, higher patient throughput can be achieved, however weather variability can introduce uncertainty in patient scheduling and the received light dose.

Clinical adoption of PDT can be expanded by demonstrating a low-cost mobile phone based system for efficiently planning and monitoring treatments of non-melanoma skin cancers (NMSC) and pre-cancerous actinic keratosis (AK). This can be achieved by the ability to easily plan and monitor PDT treatments without the need for an expensive treatment lamp, thus allowing for future treatments to occur at non-specialist medical facilities which are more easily accessible to a larger patient demographic. Applicants' platform provides the capability to collect data regarding light dose and PpIX production which can be leveraged to help define guidelines for future mobile-outreach clinics or at-home application.

Example 3.1. Treatment Planning

Figure 15A:
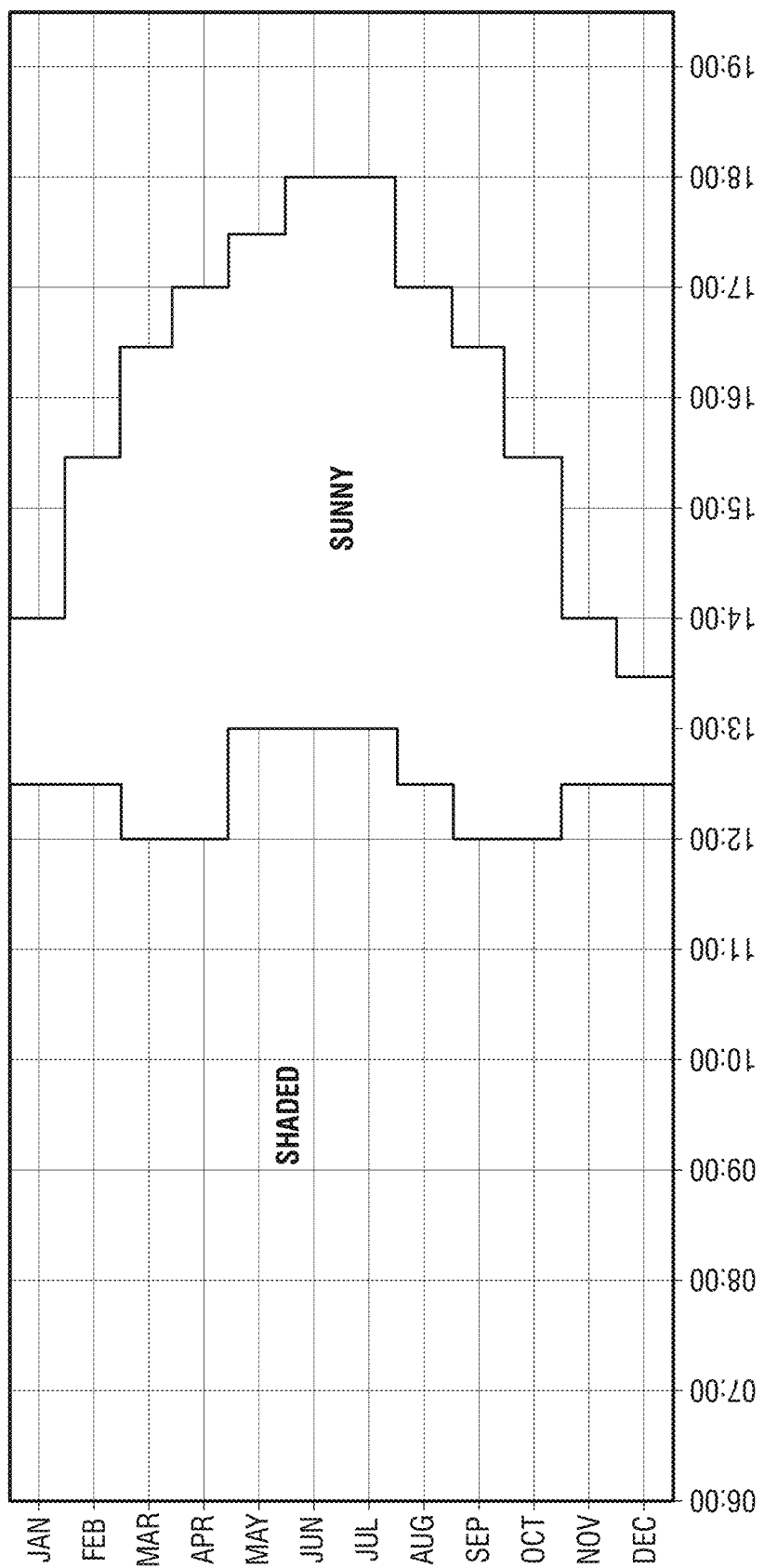
FIGS. 15A, 15B, and 15C illustrate an example one-time site assessment that can be used to determine appropriate sites for daylight-PDT treatments throughout the year (FIG. 15A). Spectroradiometer measurements can be integrated to show the weather-dependent irradiance fluctuations (FIG. 15B) which can then be correlated with real-time local weather reports, demonstrating a high correlation (FIG. 15C).
Figure 15B:
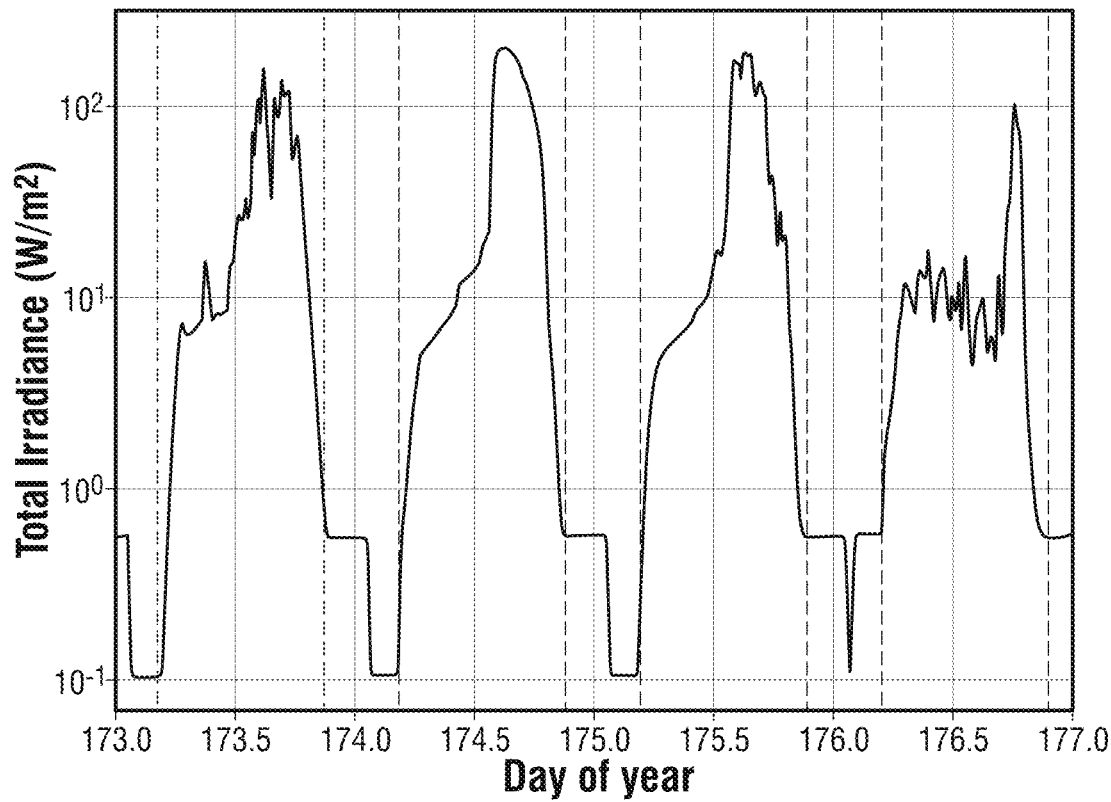

A simple single-time site assessment of a location can identify two characteristics of the site: (1) the seasonal fluctuations in daylight; and (2) the spectral characteristics introduced by barriers such as windows. Using tools commonly used in the photovoltaic industry, the hourly changes in daylight due to obstructions and seasonal variability can be recorded and used for long-term patient scheduling (FIG. 15A). Protection against harmful UV light is of importance, especially in the treated populations. As such, chemical sunscreen or UV-blocking glass are recommended for daylight-PDT treatments.

The measurements of spectral transmission through glass can be used as an input to a centralized dose-planning database. A database can be created based on Monte Carlo models of broad-spectrum light fluence through a multi-layer skin model. The models presented herein provide for such a system, which, in some instances, can use an on demand cloud-based modeling infrastructure, which can be easily modified to consider different levels of pigmentation or disease morphology. The result of this modeling, in some instances, is a lookup-table providing the minimum treatment time based on lesion thickness, irradiance intensity and incubation time of the ALA.

Figure 15C:
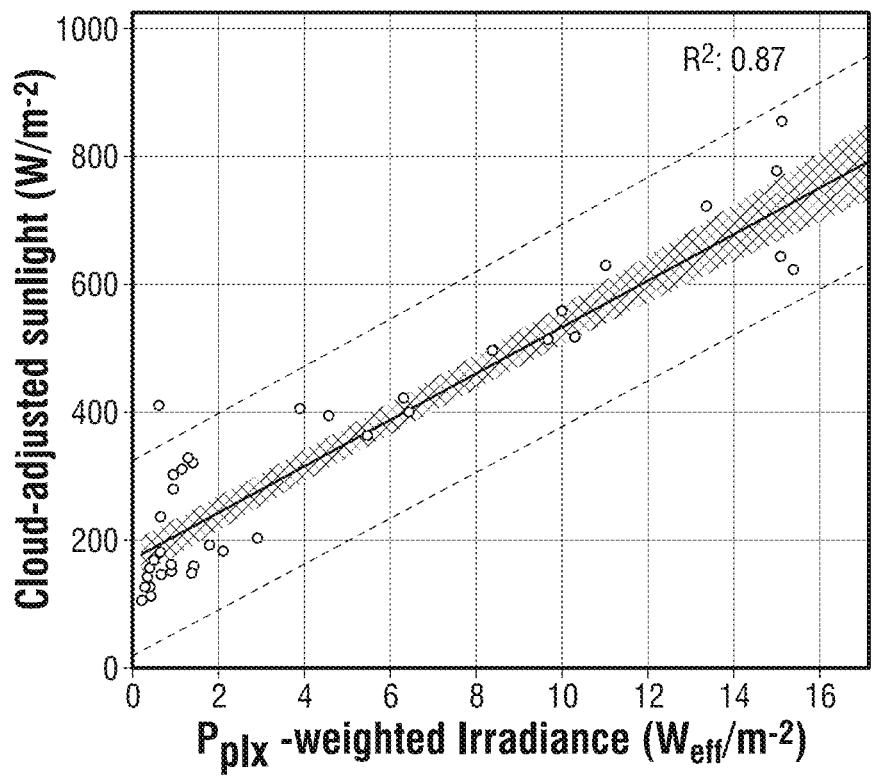

Using location services provided by a mobile device, current weather conditions and forecasts can be accessed and such systems have shown high correlation between weather reports and measured irradiance (FIG. 15C). This information can be used as a surrogate for irradiance measurements in the treatment lookup table process. Through development of an application programing interface (API) the complexity of using these model-based lookup tables in conjunction with current weather reports can be drastically simplified and automated, providing dose plans with a few button clicks.

Example 3.2. Treatment Monitoring

Figure 16:
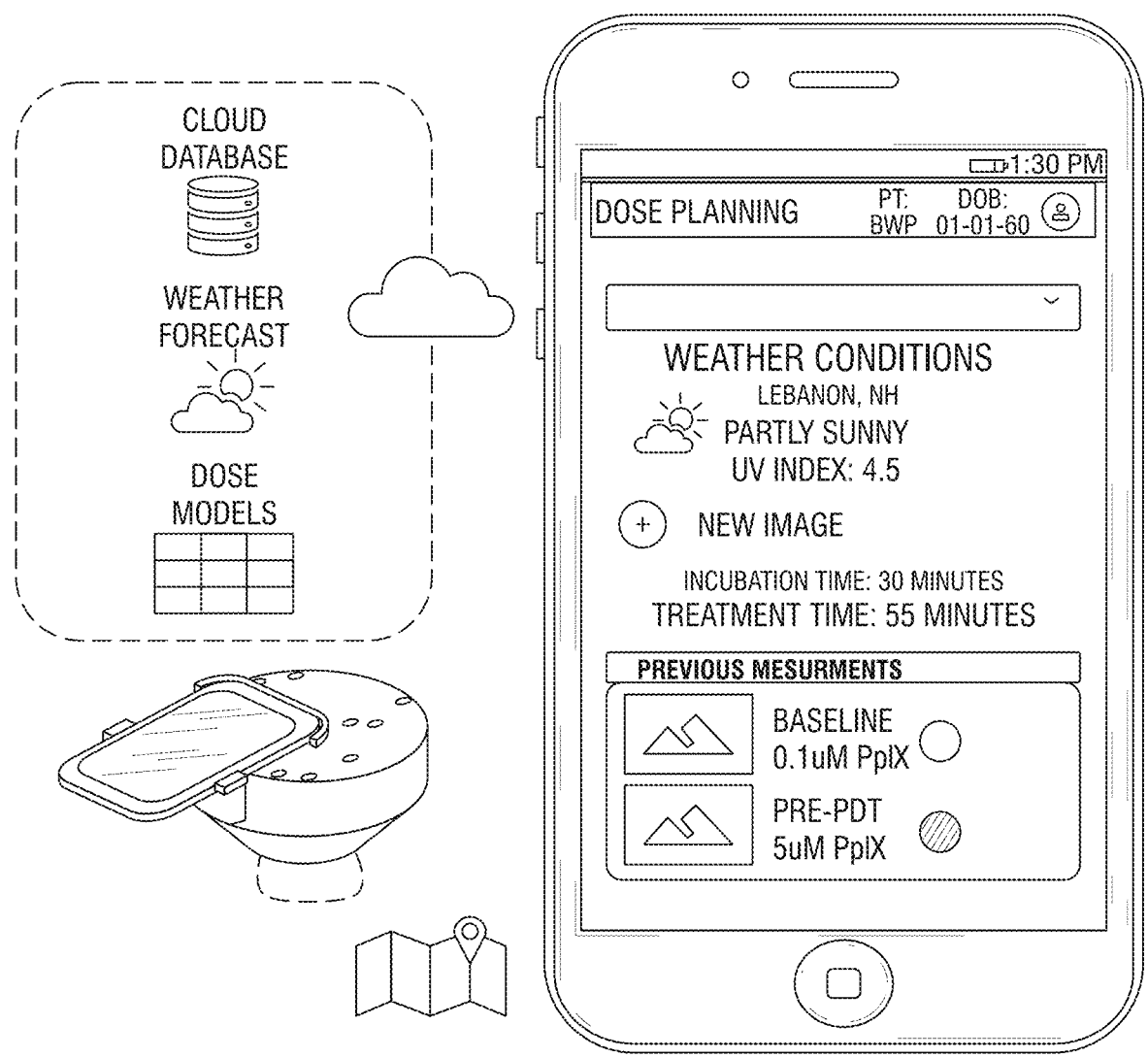
FIG. 16 illustrates an example mobile phone based treatment planning and monitoring system according to an aspect of the present disclosure. The mobile phone can collect location information and fluorescence measurements to be used with a web-accessible treatment planning model.

Since PpIX produces fluorescence emissions when activated, indirect dosimetry can be achieved by monitoring trends in the fluorescent signal. Through further development of Applicants' treatment planning and monitoring system, the complexities of daylight-PDT treatments can be reduced (FIG. 16). The automation implemented in the systems aim to provide the quantifiable rigor needed for treatment replication, which is important as more daylight-PDT studies are conducted, while also opening this treatment modality to a wider population. Since an expensive clinical lamp is not needed for treatment, and Applicants' design utilizes a small form-factor smartphone, treatments can be conducted anywhere there is enough sunlight. Currently, diagnosis and treatment of AKs requires at least two trips to a dermatologist, however, the systems demonstrated herein can provide the ability to eliminate a second trip to a specialist and instead be treated at their nearest community health facility, or through mobile outreach services.

While the current system design utilizes a centralized treatment planning database, this data can also be cached on the phone for treatment in areas without internet connection. Through secure data transfer, both white-light and dosimetric images of lesions can be recorded for entry in an electronic medical record (EMR) system. While many daylight-PDT studies currently record whether it was sunny or cloudy, there is very little information available on the transient weather conditions and total fluence received by the patient. This can be addressed using time-resolved measurements of weather fluctuations resulting in changes in fluence rate, which can be transferred to the EMR through the system API. This mechanism provides the opportunity to quantitatively monitor daylight PDT treatments and provide insight on methods to further optimize this treatment modality.

Example 3.3. Weather-Informed Model-Based Dose Planning in a Mobile Application

Monte Carlo models of multilayer skin geometries have been developed utilizing a wide spectral range of optical inputs. These models provide insight into the amount of light available to activate PpIX. Through combining these models with estimates of ALA diffusion and PpIX production rates, a time-resolved estimate of photodynamic dose can be achieved. Categories of skin pigmentation and lesion morphologies can be defined, and the resulting model-based light fluence estimates can be tabulated. This information can be combined in a web-accessible database combined with estimates ALA diffusion and PpIX production rates. The centralized database can also store characteristics of treatment locations, such as spectral transmission of barrier glass used during indoor treatments. Through a one-time site assessment, the spectral characteristics can be stored as a property of the registered location in the database, which can be used to scale the generic light-fluence models. An API can programmatically access this information from a front-end mobile application. In some instances, additional logic to cache subsets of the modeled data can enable offline treatment planning. The API can also allow for treatment progress to be recorded and shared with external EMR systems.

FIG. 16 illustrates a mobile phone based treatment planning and monitoring system according to an aspect of the present disclosure. The mobile phone can collect location information and fluorescence measurements to be used with a web-accessible treatment planning model.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of determining optimal parameters for application of light from a light source to a tissue, said method comprising:
utilizing an algorithm to generate results related to estimating light flow from the light source into the tissue;
utilizing the results to determine optimal parameters for applying the light source to the tissue; and
applying the light source to the tissue using the optimal parameters, wherein the application of the light source occurs in the presence of a photosensitive compound.

2. The method of claim 1, wherein the algorithm is selected from the group consisting of a Monte Carlo model, a broad-spectrum light fluence model, a Monte Carlo model of broad-spectrum light fluence, optical radiative transport models, optical diffusion models, and combinations thereof.

3. The method of claim 1, wherein the algorithm comprises a seven-layer skin model comprising at least one of stratum corneum layers, living epidermis layers, papillary dermis layers, upper blood net dermis layers, reticular dermis layers, deep blood dermis layers, and subcutaneous fat layers.

4. The method of claim 1, wherein the algorithm utilizes at least one factor to estimate the light flow, wherein the at least one factor is selected from the group consisting of type of the light source, position of the light source, light fluence from the light source, location specific information, models of diffusion kinetics and spectral absorption characteristics of a photosensitive compound of interest, melanin content of the tissue, thickness of the tissue, thickness of a lesion on the tissue, pigmentation, actinic keratosis thickness, spectrally-resolve attenuation introduced by topical applications to tissue, and combinations thereof.

5. The method of claim 4, wherein the at least one factor comprises location specific information, wherein the location specific information comprises weather forecast, cloud coverage, ultra-violet index, elevation, temperature, barometric pressure, atmospheric pressure, chance of precipitation, humidity, relative humidity, wind speed, wind direction, air quality, average air particulate size, spectrally-resolve attenuation introduced by physical barriers, and combinations thereof.

6. The method of claim 1, wherein at least a portion of the results are generated via at least one method comprising estimating effective fluence rates, comparing the fluence rates between multiple broadband and narrowband sources, estimating effective fluence rates for multi-layer tissue models of varying geometry and optical properties, analyzing production of a photosensitive compound, analyzing photobleaching of a photosensitive compound, generating an effective total fluence for various treatment times, determining a dynamic dose range, and combinations thereof.

7. The method of claim 6, wherein at least a portion of the results are generated via at least estimating effective fluence rates, and wherein the estimating effective fluence rates comprises utilizing tissue optical properties.

8. The method of claim 7, wherein the tissue optical properties are at least one property comprising refraction, polarization, reflection, absorption, photoluminescence, transmittance, diffraction, dispersion, dichroism, scattering, anisotropy, birefringence, color, photosensitivity, optical properties attributed to melanin, and combinations thereof.

9. The method of claim 6, wherein at least a portion of the results are generated via comparing the fluence rates between multiple broadband and narrowband sources, and wherein the comparing the fluence rates between multiple broadband and narrowband sources utilizes data comprising narrowband sources modeled based on clinically available sources, broadband sources based on measurements taken by a spectroradiometer, and combinations thereof.

10. The method of claim 6, wherein at least a portion of the results are generated via analyzing production and photobleaching of a photosensitive compound.

11. The method of claim 10, wherein the photosensitive compound is protoporphyrin IX (PpIX).

12. The method of claim 10, wherein analyzing production and photobleaching of the photosensitive compound utilizes data comprising diffusion rate of a prodrug, diffusion rate of a drug, rate and efficiency that a prodrug is converted to the photosensitive compound, rate and efficiency that a drug is converted to the photosensitive compound, estimated photobleaching data, and combinations thereof.

13. The method of claim 12, wherein the estimated photobleaching data comprises at least one of initial photosensitive compound concentration, fluence rate, a photosensitive compound weighted effective fluence rate, and a photobleaching constant.

14. The method of claim 6, wherein at least a portion of the results are generated via generating an effective total fluence for various treatment times, and wherein the generating the effective total fluence for various treatment times comprises identifying at least one of a treatment time and incubation time based on an initial depth distribution of a photosensitive compound.

15. The method of claim 6, wherein at least a portion of the results are generated via generating an effective total fluence for various treatment times, and wherein the generating the effective total fluence for various treatment times depends on a spectrum and fluence rate of the light.

16. The method of claim 6, wherein at least a portion of the results are generated via determining a dynamic dose range, and wherein the dynamic dose range is determined from data comprising initial incubation times, estimated ignition incubation times, surface irradiation values, estimated irradiation values, a range of surface irradiation values, an estimated range of surface irradiation values, and combinations thereof.

17. The method of claim 6, wherein at least a portion of the results are generated via determining a dynamic dose range, and wherein the dynamic dose range is determined from a light source fluence rate at depths in the tissue that are linearly scaled to represent a range of surface irradiation values.

18. The method of claim 6, wherein at least a portion of the results are generated via determining a dynamic dose range, and wherein the determining the dynamic dose range comprises identifying an effective photodynamic dose, and wherein the effective photodynamic dose is defined as a product of threshold effective fluence and photosensitive compound concentration.

19. The method of claim 1, wherein the results comprise light flow into the tissue, a photodynamic dose for a photosensitive compound at depths into the tissue, sunlight available at depths into the tissue, treatment dose for a photosensitive compound, minimum time needed to reach a threshold photodynamic dose, and combinations thereof.

20. The method of claim 1, wherein the results comprise a chart to prescribe minimal treatment times to achieve depth-dependent cytotoxic effect based on incubation times and irradiance values for a plurality of light sources.

21. The method of claim 20, where the chart provides an estimate of depth of potential photosensitive compound activation as a function of treatment time for each light source of the plurality of light sources.

22. The method of claim 20, wherein the chart comprises clinically relevant dose planning information used to define treatment times required to achieve activation at specific depths for each light source of the plurality of light sources over a range of irradiance values and photosensitive compound incubation times.

23. The method of claim 20, wherein the chart comprises data comprising indications of seasons most commonly associated with given irradiance for various latitudes, lesion type, estimated depth, melanin content, photosensitive compound production rate, and combinations thereof.

24. The method of claim 1, wherein the determined optimal parameters comprise a light source type, a dosage, a minimum treatment time, a maximum treatment time, a recommended exposure time, daylight hours for optimal treatment, sunlight hours for optimal treatment, location for optimal sunlight exposure, location for optimal daylight exposure, light flow into the tissue, effective fluence rates for the tissue, a total treatment time based on a correlation of the light flow into the tissue and the effective fluence rates, feedback mechanisms based on measurements of photosensitizer production and photobleaching, and combinations thereof.

25. The method of claim 1, wherein the determined optimal parameters comprise:
light flow into the tissue;
effective fluence rates for the tissue; and
a total treatment time based on a correlation of the light flow into the tissue and the effective fluence rates.

26. The method of claim 1, wherein the light source comprises daylight, sunlight, simulated light, simulated daylight, simulated sunlight, naturally generated light, artificially generated light, natural light generated by the sun, artificial light generated by a halogen light, a compact fluorescent lamp light, a light emitting diode (LED) light, a blue LED light, a red LED light, a white light, or a lamp light, broad-spectrum light, narrow-spectrum light, broadband light, narrowband light, and combinations thereof.

27. The method of claim 1, wherein the estimated light flow of the light source into the tissue is based on a theoretical uniform spectrum of light.

28. The method of claim 1, wherein the tissue is skin tissue comprising at least one of a tumor site, non-melanoma skin cancer, a lesion site, actinic keratosis, hypertrophic actinic keratosis, squamous cell carcinoma, invasive squamous cell carcinoma, basal cell carcinoma (superficial type), basal cell carcinoma (nodular type), acne vulgaris, rhinophyma, wrinkles, sun-damage, and combinations thereof.

29. The method of claim 1, wherein the tissue is skin, and wherein the skin comprises layers selected from the group consisting of a stratum corneum layer, a living epidermis layer, a papillary dermis layer, an upper blood net dermis layer, a reticular dermis layer, a deep blood dermis layer, a subcutaneous fat layer, or combinations thereof.

30. The method of claim 1, wherein the photosensitive compound is protoporphyrin IX (PpIX).

31. The method of claim 1, wherein the application of the light source is utilized to treat a condition associated with the tissue.

32. The method of claim 31, wherein the tissue is skin, and wherein the method is utilized to treat a condition associated with the skin.

33. The method of claim 32, wherein the condition is selected from the group consisting of a skin tumor, non-melanoma skin cancer, a lesion site, actinic keratosis, hypertrophic actinic keratosis, squamous cell carcinoma, invasive squamous cell carcinoma, basal cell carcinoma (superficial type), basal cell carcinoma (nodular type), acne vulgaris, rhinophyma, wrinkles, sun-damage, and combinations thereof.

* * * * *